US010429392B2

(12) United States Patent
Sahin et al.

(10) Patent No.: US 10,429,392 B2
(45) Date of Patent: Oct. 1, 2019

(54) METHODS AND COMPOSITIONS FOR DIAGNOSIS AND TREATMENT OF CANCER

(71) Applicants: BioNTech RNA Pharmaceuticals GmbH, Mainz (DE); TRON—TRANSLATIONALE ONKOLOGIE AN DER UNIVERSITÄTSMEDIZIN DER JOHANNES GUTENBERG-UNIVERSITÄT MAINZ GEMEINNÜTZIGE GMBH, Mainz (DE)

(72) Inventors: Ugur Sahin, Mainz (DE); Claudia Paret, Mainz (DE); Christian Bender, Mainz (DE); Kirsten Vormbrock, Hamburg (DE); Diana Barea Roldan, Mainz (DE); Stefanie Hubich, Nierstein (DE); Christoph Hartmann, Frankfurt (DE)

(73) Assignees: BIONTECH RNA PHARMACEUTICALS GMBH, Mainz (DE); TRON—TRANSLATIONALE ONKOLOGIE AN DER UNIVERSITAT, Mainz (DE)

(*) Notice: Subject to any disclaimer, the term of this patent is extended or adjusted under 35 U.S.C. 154(b) by 19 days.

(21) Appl. No.: 15/518,586

(22) PCT Filed: Oct. 19, 2015

(86) PCT No.: PCT/EP2015/074136
§ 371 (c)(1),
(2) Date: Apr. 12, 2017

(87) PCT Pub. No.: WO2016/062659
PCT Pub. Date: Apr. 28, 2016

(65) Prior Publication Data
US 2017/0276681 A1 Sep. 28, 2017

(30) Foreign Application Priority Data
Oct. 20, 2014 (WO) ................ PCT/EP2014/072419

(51) Int. Cl.
| | | |
|---|---|---|
| *G01N 33/574* | (2006.01) |
| *C07K 16/30* | (2006.01) |
| *A61K 35/17* | (2015.01) |
| *A61K 38/03* | (2006.01) |
| *A61K 48/00* | (2006.01) |
| *C07K 14/47* | (2006.01) |
| *C12Q 1/6886* | (2018.01) |
| *G01N 33/50* | (2006.01) |

(52) U.S. Cl.
CPC ....... *G01N 33/57484* (2013.01); *A61K 35/17* (2013.01); *A61K 38/03* (2013.01); *A61K 48/005* (2013.01); *C07K 14/4747* (2013.01); *C07K 16/30* (2013.01); *C12Q 1/6886* (2013.01); *G01N 33/5011* (2013.01); *G01N 33/57407* (2013.01); *G01N 2800/52* (2013.01)

(58) Field of Classification Search
CPC ................ A61K 31/713; C12Q 1/6886; C12Q 2600/158; G01N 33/57415
USPC ......... 435/6.1, 6.11, 6.12, 6.13, 91.1, 91.31; 514/44; 536/23.1
See application file for complete search history.

(56) References Cited

U.S. PATENT DOCUMENTS

2018/0105883 A1* 4/2018 Lieberman ........... C12Q 1/6886

FOREIGN PATENT DOCUMENTS

| WO | WO2011051276 | 5/2011 | |
| WO | WO-2011051276 A1 * | 5/2011 | ....... G01N 33/57419 |
| WO | WO2011051278 | 5/2011 | |
| WO | WO-2011051278 A1 * | 5/2011 | ......... C07K 16/3023 |
| WO | WO2011051280 | 5/2011 | |
| WO | WO2012031122 | 3/2012 | |

OTHER PUBLICATIONS

Uhlen et al, Molecular and Cellular Proteomics, vol. 4.12, pp. 1920-1932. (Year: 2005).*
Uhlen et al., Expression of COL2A1 in Cancer—Summary, The Human Protein Atlas, pp. 1-3. (Year: 2005).*
International Search Report and Written Opinion for PCT/EP2015/074136 dated Jan. 8, 2016.

* cited by examiner

*Primary Examiner* — Jane J Zara
(74) *Attorney, Agent, or Firm* — Neal, Gerber & Eisenberg LLP; Kevin A. O'Connor

(57) ABSTRACT

The present invention relates to the identification of nucleic acid and amino acid sequences that are characteristic of tumor tissues, in particular tumors of the central nervous system (CNS) such as glioma, in particular glioblastoma and which represent targets for therapy or diagnosis of tumor diseases in a subject.

Figure 1:
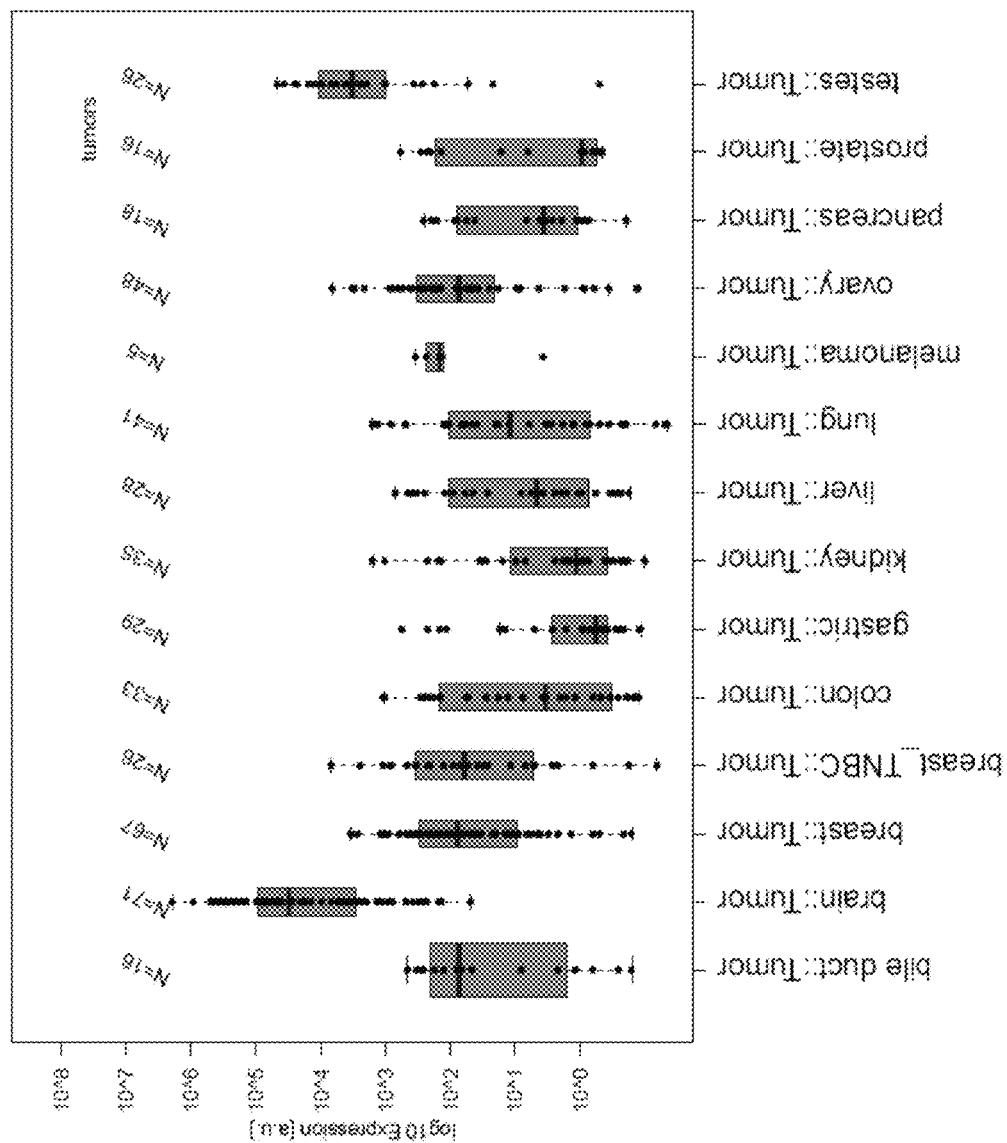

13 Claims, 7 Drawing Sheets
Specification includes a Sequence Listing.

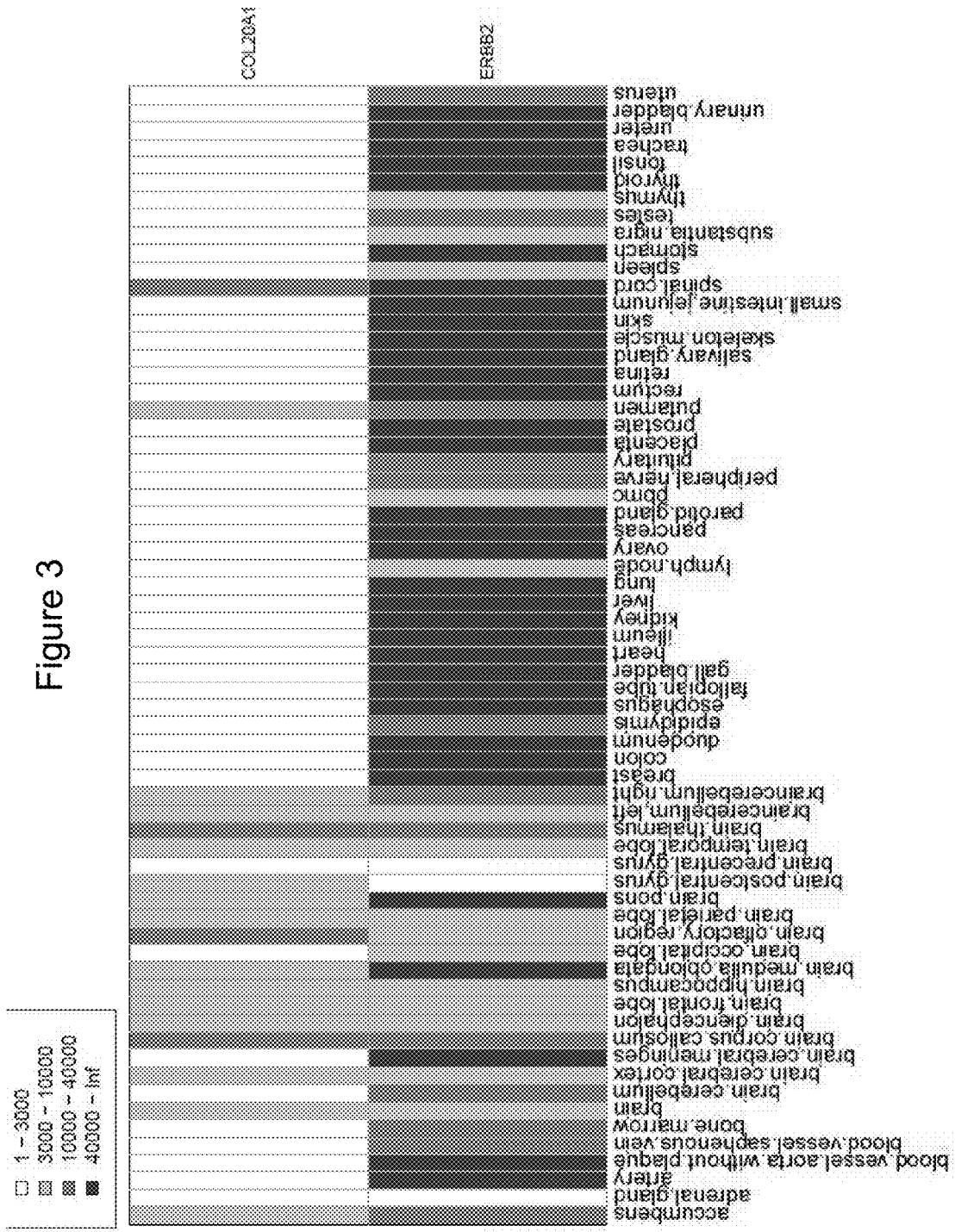

Figure 4A

| | Description | Max score | Identity | Accession |
|---|---|---|---|---|
| Select seq ref\|NP_066933.1\| | collagen alpha-1(XIV) chain precursor [Homo sapiens] | 454 | 35% | NP_066933.1 |
| Select seq ref\|XP_005251116.1\| | PREDICTED: collagen alpha-1(XIV) chain isoform X1 [Homo sapiens] | 453 | 35% | XP_005251116.1 |
| Select seq ref\|NP_542376.2\| | collagen alpha-1(XII) chain short isoform precursor [Homo sapiens] | 425 | 37% | NP_542376.2 |
| Select seq ref\|XP_006715397.1\| | PREDICTED: collagen alpha-1(XII) chain isoform X1 [Homo sapiens] | 424 | 37% | XP_006715397.1 |
| Select seq ref\|NP_000085.1\| | collagen alpha-1(VII) chain precursor [Homo sapiens] | 239 | 34% | NP_000085.1 |
| Select seq ref\|XP_006715286.1\| | PREDICTED: collagen alpha-1(XXI) chain isoform X5 [Homo sapiens] | 150 | 29% | XP_006715286.1 |
| Select seq ref\|NP_110447.2\| | collagen alpha-1(XXI) chain precursor [Homo sapiens] | 149 | 29% | NP_110447.2 |
| Select seq ref\|XP_006715287.1\| | PREDICTED: collagen alpha-1(XXI) chain isoform X6 [Homo sapiens] | 143 | 29% | XP_006715287.1 |
| Select seq ref\|XP_006716576.1\| | PREDICTED: collagen alpha-1(XXII) chain isoform X2 [Homo sapiens] | 143 | 41% | XP_006716576.1 |
| Select seq ref\|NP_690848.1\| | collagen alpha-1(XXII) chain precursor [Homo sapiens] | 142 | 41% | NP_690848.1 |
| Select seq ref\|XP_005250867.1\| | PREDICTED: collagen alpha-1(XXII) chain isoform X1 [Homo sapiens] | 142 | 41% | XP_005250867.1 |

Figure 4B

Figure 5

| Aa Pos | sequence | score |
|---|---|---|
| 346 | ALAGLLSRL | 31 |
| 275 | GLRPEAAKV | 27 |
| 369 | AAAPALDTL | 26 |
| 839 | SLPGFDLMV | 26 |
| 1227 | KLEPGTEPL | 26 |
| 933 | LLDAGKKSL | 25 |
| 1193 | SLATLYQLV | 25 |
| 182 | FLVDGSWSI | 24 |
| 302 | VLKDLGVNV | 24 |
| 305 | DLGVNYFAV | 24 |
| 435 | NLASRTEYL | 24 |
| 453 | GVGEGLRGL | 24 |
| 457 | GLRGLVTTA | 24 |
| 549 | GIRARTPTL | 24 |
| 52 | SGLGYLVQV | 23 |
| 104 | FLLARREFV | 23 |
| 197 | QVKDFLASV | 23 |
| 235 | SLSTKEQVL | 23 |
| 325 | LLASPPRDI | 23 |

| Aa Pos | sequence | score |
|---|---|---|
| 342 | LQLGALAGL | 23 |
| 376 | TLPAPISLV | 23 |
| 731 | SLRYTPSTV | 23 |
| 882 | QLTRRYSDV | 23 |
| 899 | HTIVFLVRL | 23 |
| 903 | FLVRLLPET | 23 |
| 983 | RLYVDCRKV | 23 |
| 105 | LLARREFVI | 22 |
| 438 | SRTEYLVSV | 22 |
| 669 | AAAPSGVLV | 22 |
| 900 | TIVFLVRLL | 22 |
| 72 | ILTTKIPKA | 21 |
| 343 | QLGALAGLL | 21 |
| 428 | AASTELHNL | 21 |
| 477 | AVTPRTVHL | 21 |
| 657 | ELPGDAVQL | 21 |
| 809 | VLVSAIYAA | 21 |
| 815 | YAAGRSEAV | 21 |
| 854 | KAYASIRGV | 21 |

| Aa Pos | sequence | score |
|---|---|---|
| 1008 | VTLGRLAKA | 21 |
| 1023 | SAAFQLQML | 21 |
| 1137 | RGLEGTAGL | 21 |
| 12 | CLWLWLGAT | 20 |
| 26 | VQASGLLRL | 20 |
| 29 | SGLLRLAVL | 20 |
| 228 | QTEWDLNSL | 20 |
| 241 | QVLAAYRRL | 20 |
| 307 | GVNVFAVGV | 20 |
| 475 | LAAVTPRTV | 20 |
| 521 | VLLDGLEPG | 20 |
| 579 | GAPRPYRLV | 20 |
| 608 | ATSATLGPL | 20 |
| 749 | LASETPDSL | 20 |
| 844 | DLMVAESLV | 20 |
| 907 | LLPETPREA | 20 |
| 928 | PLLGVLLDA | 20 |
| 974 | HVAVGRSKV | 20 |
| 1196 | TLYQLVSQA | 20 |
| 1199 | QLVSQASHV | 20 |

SEQUENCE LISTING

```
<160> NUMBER OF SEQ ID NOS: 64

<210> SEQ ID NO 1
<211> LENGTH: 4187
<212> TYPE: DNA
<213> ORGANISM: Homo sapiens

<400> SEQUENCE: 1
ataagctcca gccttcctgt ggccacagca ggaccagagt ggaccagcac accccaggag      60
agaggactgg ggtcccagga gtaggaggag cccgagcacc atgagctccg gagaccctgc     120
acacctcggc ctctgcctct ggctgtggct gggcgccacc ctgggaagag agcaagttca     180
agcaagcggt ctcctgaggc tggctgtgct gcctgaggac cggctgcaga tgaagtggag     240
```

```
agagtcggag gggagcggcc tcggctacct ggtgcaggtg aagcccatgg caggggactc      300
ggaacaggag gtgatactga ccaccaagac ccctaaggcc acagtggggg gcctgagccc      360
ctccaagggc tacaccttgc agatcttcga gctcactggc tctggcgct tcctgctagc      420 tcggaggag tttgtgattg aggatctgaa gagtagctcc ctggacagga gcagccagag      480
gcccctcggc tctggagccc cggagcccac ccctcccac acggggagcc cagaccctga      540
gcaggcttct gagccccaag ttgccttcac accaagccag gatccgcgca ctcctgccgg      600
cccccagttc cgctgcctgc ccccgtgcc tgctgacatg gtcttcctgg tggacgggtc      660
ctggagcatt ggccacagtc acttccagca ggtcaaggac ttcctggcca gtgtcatcgc      720
accctttgaa atcgggccgg ataaggtcca agtaggcctg actcagtaca gcggggatgc      780
tcagactgag tgggacctga actccctcag caccaaggaa caggtgctgg cagctgtgcg      840
ccgcctccgc tacaaggggg ggaacacgtt cacaggcctt gccctgaccc acgtgctggg      900
gcagaacctg cagccggcgg ctggcctccg tccagaggca gccaaggtgg tgattctggt      960
gacggacggc aagtcccagg acgatgtgca cactgctgcc cgtgtcctca aggacctggg     1020
cgtgaacgtc ttcgctgtgg gtgtgaagaa cgccgatgag gctgagctga ggctcctggc     1080
gtccccgccg agggacatca ccgtccacag cgtgctggac ttcctgcagc tcggcgcgct     1140
ggctggcctg ctcagccgtc tcatctgcca gaggctccag ggtgggagcc cgcggcaggg     1200
cccagcagcg gctccagccc tggacaccct ccctgccccc accagcctgg tcctgagcca     1260
ggtgacctcc tccagcatcc gcctgtcctg gactccagcc cccggcacc ccctcaagta     1320 tctgatcgtt tggcgagcct ctagaggtgg caccccagg gaggtggtgg tggagggacc     1380
cgccgcctcc acggagctgc acaacctggc ctcccgcaca gagtacctgg tctccgtgtt     1440
ccccatctat gagggcgggg ttggcgaagg cctgcgggc ctggtgacca cagcacctct     1500
gcctccgccc cgggcgctga ccctggccgc agtgacgccc agaaccgtcc acctcacctg     1560
gcagccctcg gccggggcca cccactacct ggtgcgatgt tctcctgctt ccccaagggg     1620
tgaagaggag gagcgagagg tgcaggtcgg gcggcccgag gtgctgctgg atggcctgga     1680
acctggcagg gactatgagg tctcggtgca gagcctgcga ggccctgagg cagcgaggc     1740 ccggggcatc cgtgccagga cccccaccct ggcccccccg agacacctgg gcttctcaga     1800
cgtgagccac gacgcggcac gagtgttctg ggagggtgcc ccgaggcctg tgcgcctggt     1860
cagggtcacc tatgtgtcca gcgagggtgg acactcgggg cagacagagg ctcctgggaa     1920
cgccacctcg gccacgctgg ggcctctctc ttcctccacc acctacactg tccgtgtcac     1980
ctgcctctac cctgggggtg gctcctctac gctgactggc cgggtgacca ccaagaaagc     2040
tcccagccca agccagctgt ccatgacgga gctgccaggg gatgcagtcc agctggcgtg     2100
ggtggccgca gcccgtctg gcgtgcttgt ctaccagatc acgtggacgc ccctgggaga     2160
ggggaaggct cacgagatct ctgtcccagg gaacctcggc acggccgtcc tgcctggcct     2220
agggaggcac acagagtacg acgtcaccat cttggcctac tacaggacg gggcccgcag     2280 tgaccctgtg tccctccgct ataccccctc cacggtgagc aggagcccac cctccaacct     2340
ggccctggcc tcggagaccc ccacagcct gcaggtcagc tggacgcccc gcttggccg     2400 cgtgctccat tactggctca cctacgcccc cgcctctggc ttgggacccg agaaatccgt     2460
ctctgtgcca ggagccagga gccacgtgac actgccgac ctgcaggcag ccacgaagta     2520
cagggtcctg gtctcagcta tctatgcagc aggcaggagt gaggctgtgt ctgccacggg     2580
ccagacagcc tgcccagccc tccgccctga cggctcccct ccagggtttg acctgatggt     2640
```

```
ggccttcagc ctggtggaaa aggcttatgc gtccatccgg ggcgtggcca tggagccctc    2700
tgccttcggt gggaccccga ccttcacgct cttcaaggac gcccagctga caagacgggt    2760
cagtgacgtc tacccagccc ccctacctcc agagcacacc atcgtcttcc ttgtgcgcct    2820
acttcccgag acaccccgtg aggccttcgc gctgtggcag atgacagccg aggacttcca    2880
gcccctcctt ggggttctgc tggatgccgg gaagaagtcc ctgacctact tccaccgtga    2940
ccccagggct gccttgcagg aggccaccct cgacccgcag gaagtgagga agattttctt    3000
cgggagcttc cacaaggtgc acgtggctgt gggccgctcc aaggtcaggc tctatgtgga    3060
ctgccggaag gtggctgagc ggccccttgg ggagatgggc agcccacccg ctgcgggctt    3120
cgtcacgctg ggaggctgg ccaaggccag ggcccccgg agcagttcgg ccgcgtttca    3180
gctccagatg ctgcagatcg tgtgcagtga cacctgggcc gatgaggacc ggtgctgtga    3240
gctccctgcc tcgagggatg agagacctg ccccgccttc gtgtctgcct gttcctgttc    3300
ctcagagacc cctgggcccc caggacctca aggaccccca ggcctccctg ggaggaatgg    3360
caccccagga gagcagggct tcccagggcc caggggtcca ccagggtca aggagagaa    3420 gggagaccat gggcttccag gcttgcaggg ccaccccggc caccagggca tcccgggag    3480 agttggcctc cagggaccaa agggaatgag aggcctggag ggaactgctg gcctgcctgg    3540
accccctggc cccaggggt tccagggcat ggcaggggcc aggggcacta gtggagagcg    3600
aggacctcca gggaccgtgg ggcccacagg actgccaggg cccaaagggg aacgaggaga    3660
gaagggcgag ccgcagtccc ttgccaccct ctaccagctt gtgagccagg cctcacacgt    3720
gtcaaagttc gactccttcc acgagaacac caggccccc atgcccatct ggagcagaa    3780 gctggagccg gcactgagc ccctgggggt ccctggcacc cgcagcaagg ccctggttcc    3840
tggagaatgg gggcgtggtg gccgccacct tgagggcaga ggggagcctg gagctgttgg    3900
tcagatgggc agccctgggc agcaggggc tagcacccag ggcctctggg agtgacagga    3960 catttctgc actgccccga ggaacgctga gccttcctcc ctgggtttgt ctggacaccg    4020
agagcgacca catcctggag aagccaggag aaaagctcag gaagagcctg caggtggaag    4080
gagagggaag cagcggcctc ggccaaggcc cacccatac tcttggctct gtagcatttc    4140
caagttcaga taaaccctg agtgctcacc caaaaaaaaa aaaaaaa        4187
```

`<210>` SEQ ID NO 2  
`<211>` LENGTH: 3642  
`<212>` TYPE: DNA  
`<213>` ORGANISM: Homo sapiens

`<400>` SEQUENCE: 2

```
caccaagcca ggatccgcgc actcctggtg ggtcagagtg gagagagacc ggcccccagt     60
tccgctgcct gcccccgtg cctgctgaca tggtcttcct ggtggacggg tcctggagca    120
ttggccacag tcacttccag caggtcaagg acttcctggc cagtgtcatc gcacccttg    180 aaatcgggcc ggataaggtc caagtaggcc tgactcagta cagcggggat gctcagactg    240
agtgggacct gaactccctc agcaccaagg aacaggtgct ggcagctgtg cgccgcctcc    300
gctacaaggg ggggaacacg ttcacaggcc ttgcctgac ccacgtgctg ggcagaacc    360 tgcagccggc ggctggcctc cgtccagagg cagccaaggt ggtgattctg gtgacggacg    420
gcaagtccca ggacgatgtg cacactgctg cccgtgtcct caaggacctg ggcgtgaacg    480
tcttcgctgt gggtgtgaag aacgccgatg aggctgagct gaggctcctg gcgtccccgc    540
```

```
cgagggacat caccgtccac agcgtgctgg acttcctgca gctcggcgcg ctggctggcc    600
tgctcagccg tctcatctgc cagaggctcc agggtgggag cccgcggcag ggcccagcag    660
cggctccagc cctggacacc ctccctgccc ccaccagcct ggtcctgagc caggtgacct    720
cctccagcat ccgcctgtcc tggactccag ccccccggca cccccccaag tatctgatcg    780
tttggcgagc ctctagaggt ggcaccccca gggaggtggt ggtggaggga cccgccgcct    840
ccacggagct gcacaacctg gcctcccgca cagagtacct ggtctccgtg ttccccatct    900
atgagggcgg ggttggcgaa ggcctgcggg gcctggtgac cacagcacct ctgcctccgc    960
cccgggcgct gaccctggcc gcagtgacgc ccagaaccgt ccacctcacc tggcagccct   1020
cggccggggc cacccactac ctggtgcgat gttctcctgc ttcccccaag ggtgaagagg   1080
aggagcgaga ggtgcaggtc gggcggcccg aggtgctgct ggatggcctg aacctggca   1140
gggactatga ggtctcggtg cagagcctgc gaggccctga gggcagcgag gcccggggca   1200
tccgtgccag gaccccgacc ctggccccc cgagacacct gggcttctca gacgtgagcc   1260
acgacgcggc acgagtgttc tgggagggtg ccccgaggcc tgtgcgcctg gtcagggtca   1320
cctatgtgtc cagcgagggt ggacactcgg gcagacaga ggctcctggg aacgccacct    1380
cggccacgct ggggcctctc tcttcctcca ccacctacac tgtccgtgtc acctgcctct   1440
accctggggg tggctcctct acgctgactg gccgggtgac caccaagaaa gctcccagcc   1500
caagccagct gtccatgacg gagctgccag gggatgcagt ccagctggcg tgggtggccg   1560
cagccccgtc tggcgtgctt gtctaccaga tcacgtggac gcccctggga gaggggaagg   1620
ctcacgagat ctctgtccca gggaacctcg gcacggccgt cctgcctggc ctagggaggc   1680
acacagagta cgacgtcacc atcttggcct actacaggga cggggcccgc agtgaccctg   1740
tgtccctccg ctatacccc tccacggtga gcaggagccc accctccaac ctggccctgg    1800
cctcggagac ccccgacagc ctgcaggtca gctggacgcc cccgcttggc cgcgtgctcc   1860
attactggct cacctacgcc cccgcctctg gcttgggacc cgagaaatcc gtctctgtgc   1920
caggagccag gagccacgtg acactgcccg acctgcaggc agccacgaag tacagggtcc   1980
tggtctcagt tatctatgca gcaggcagga gtgaggctgt gtctgccacg gccagacag    2040
cctgcccagc cctccgccct gacggctccc tcccagggtt tgacctgatg gtggccttca   2100
gcctggtgga aaaggcttat gcgtccatcc ggggcgtggc catggagccc tctgccttcg   2160
gtgggacccc gaccttcacg ctcttcaagg acgcccagct gacaagacgg gtcagtgacg   2220
tctacccagc cccctacct ccagagcaca ccatcgtctt ccttgtgcgc ctacttcccg    2280
agacaccccg tgaggccttc gcgctgtggc agatgacagc cgaggacttc agcccctcc    2340
ttggggttct gctggatgcc gggaagaagt ccctgaccta cttccaccgt gaccccaggg   2400
ctgccttgca ggaggccacc ttcgacccgc aggaagtgag gaagattttc ttcgggagct   2460
tccacaaggt gcacgtggct gtgggccgct ccaaggtcag gctctatgtg gactgccgga   2520
aggtggctga gcggcccctt ggggagatgg gcagcccacc cgctgcgggc ttcgtcacgc   2580
tggggaggct ggccaaggcc aggggccccc ggagcagttc ggccgcgttt cagctccaga   2640
tgctgcagat cgtgtgcagt gacacctggg ccgatgagga ccggtgctgt gagctccctg   2700
cctcgaggga tggagagacc tgccccgcct tcgtgtctgc ctgttcctgt tcctcagaga   2760
cccctgggcc cccaggacct caaggacccc caggcctccc tgggaggaat ggcacccag    2820
gagagcaggg cttcccaggg cccagggatc caccaggggt caaaggagag aagggagacc   2880
atgggcttcc aggcttgcag ggccaccccg gccaccaggg catccccggg agagttggcc   2940
```

-continued

```
tccagggacc aaagggaatg agaggcctgg agggaactgc tggcctgcct ggacccctg      3000
gccccagggg gttccagggc atggcagggg ccagggcac tagtggagag cgaggacctc      3060
cagggaccgt ggggcccaca ggactgccag ggcccaaagg ggaacgagga gagaagggcg     3120
agccgcagtc ccttgccacc ctctaccagc ttgtgagcca ggcctgtgag tctgccattc     3180
agacacacgt gtcaaagttc gactccttcc acgagaacac caggcccccc atgcccatct     3240
tggagcagaa gctggagccg ggcactgagc ccctggggtc ccctggcacc cgcagcaagg     3300
ccctggttcc tggagaatgg gggcgtggtg gccgccacct tgagggcaga ggggagcctg     3360
gagctgttgg tcagatgggc agccctgggc agcagggggc tagcacccag ggcctctggg     3420
agtgacagga catttctgc actgccccga ggaacgctga gccttcctcc ctgggtttgt      3480
ctggacaccg agagcgacca catcctggag aagccaggag aaaagctcag gaagagcctg     3540
caggtggaag gagagggaag cagcggcctc ggccaaggcc caccccatac tcttggctct     3600
gtagcatttc caagttcaga taaacccctg agtgctcacc ca                       3642
```

<210> SEQ ID NO 3
<211> LENGTH: 1284
<212> TYPE: PRT
<213> ORGANISM: Homo sapiens

<400> SEQUENCE: 3

```
Met Ser Ser Gly Asp Pro Ala His Leu Gly Leu Cys Leu Trp Leu Trp
1               5                   10                  15

Leu Gly Ala Thr Leu Gly Arg Glu Gln Val Gln Ala Ser Gly Leu Leu
            20                  25                  30

Arg Leu Ala Val Leu Pro Glu Asp Arg Leu Gln Met Lys Trp Arg Glu
        35                  40                  45

Ser Glu Gly Ser Gly Leu Gly Tyr Leu Val Gln Val Lys Pro Met Ala
    50                  55                  60

Gly Asp Ser Glu Gln Glu Val Ile Leu Thr Thr Lys Thr Pro Lys Ala
65                  70                  75                  80

Thr Val Gly Gly Leu Ser Pro Ser Lys Gly Tyr Thr Leu Gln Ile Phe
                85                  90                  95

Glu Leu Thr Gly Ser Gly Arg Phe Leu Leu Ala Arg Arg Glu Phe Val
            100                 105                 110

Ile Glu Asp Leu Lys Ser Ser Ser Leu Asp Arg Ser Ser Gln Arg Pro
        115                 120                 125

Leu Gly Ser Gly Ala Pro Glu Pro Thr Pro Ser His Thr Gly Ser Pro
    130                 135                 140

Asp Pro Glu Gln Ala Ser Glu Pro Gln Val Ala Phe Thr Pro Ser Gln
145                 150                 155                 160

Asp Pro Arg Thr Pro Ala Gly Pro Gln Phe Arg Cys Leu Pro Pro Val
                165                 170                 175

Pro Ala Asp Met Val Phe Leu Val Asp Gly Ser Trp Ser Ile Gly His
            180                 185                 190

Ser His Phe Gln Gln Val Lys Asp Phe Leu Ala Ser Val Ile Ala Pro
        195                 200                 205

Phe Glu Ile Gly Pro Asp Lys Val Gln Val Gly Leu Thr Gln Tyr Ser
    210                 215                 220

Gly Asp Ala Gln Thr Glu Trp Asp Leu Asn Ser Leu Ser Thr Lys Glu
225                 230                 235                 240

Gln Val Leu Ala Ala Val Arg Arg Leu Arg Tyr Lys Gly Gly Asn Thr
```

```
                245                 250                 255
Phe Thr Gly Leu Ala Leu Thr His Val Leu Gly Gln Asn Leu Gln Pro
            260                 265                 270

Ala Ala Gly Leu Arg Pro Glu Ala Ala Lys Val Val Ile Leu Val Thr
        275                 280                 285

Asp Gly Lys Ser Gln Asp Val His Thr Ala Ala Arg Val Leu Lys
    290                 295                 300

Asp Leu Gly Val Asn Val Phe Ala Val Gly Val Lys Asn Ala Asp Glu
305                 310                 315                 320

Ala Glu Leu Arg Leu Leu Ala Ser Pro Pro Arg Asp Ile Thr Val His
                325                 330                 335

Ser Val Leu Asp Phe Leu Gln Leu Gly Ala Leu Ala Gly Leu Leu Ser
            340                 345                 350

Arg Leu Ile Cys Gln Arg Leu Gln Gly Gly Ser Pro Arg Gln Gly Pro
        355                 360                 365

Ala Ala Ala Pro Ala Leu Asp Thr Leu Pro Ala Pro Thr Ser Leu Val
    370                 375                 380

Leu Ser Gln Val Thr Ser Ser Ile Arg Leu Ser Trp Thr Pro Ala
385                 390                 395                 400

Pro Arg His Pro Leu Lys Tyr Leu Ile Val Trp Arg Ala Ser Arg Gly
                405                 410                 415

Gly Thr Pro Arg Glu Val Val Glu Gly Pro Ala Ala Ser Thr Glu
            420                 425                 430

Leu His Asn Leu Ala Ser Arg Thr Glu Tyr Leu Val Ser Val Phe Pro
        435                 440                 445

Ile Tyr Glu Gly Gly Val Gly Glu Gly Leu Arg Gly Leu Val Thr Thr
    450                 455                 460

Ala Pro Leu Pro Pro Arg Ala Leu Thr Leu Ala Val Thr Pro
465                 470                 475                 480

Arg Thr Val His Leu Thr Trp Gln Pro Ser Ala Gly Ala Thr His Tyr
                485                 490                 495

Leu Val Arg Cys Ser Pro Ala Ser Pro Lys Gly Glu Glu Glu Arg
            500                 505                 510

Glu Val Gln Val Gly Arg Pro Glu Val Leu Leu Asp Gly Leu Glu Pro
        515                 520                 525

Gly Arg Asp Tyr Glu Val Ser Val Gln Ser Leu Arg Gly Pro Glu Gly
    530                 535                 540

Ser Glu Ala Arg Gly Ile Arg Ala Arg Thr Pro Thr Leu Ala Pro Pro
545                 550                 555                 560

Arg His Leu Gly Phe Ser Asp Val Ser His Asp Ala Ala Arg Val Phe
                565                 570                 575

Trp Glu Gly Ala Pro Arg Pro Val Arg Leu Val Arg Val Thr Tyr Val
            580                 585                 590

Ser Ser Glu Gly Gly His Ser Gly Gln Thr Glu Ala Pro Gly Asn Ala
        595                 600                 605

Thr Ser Ala Thr Leu Gly Pro Leu Ser Ser Ser Thr Thr Tyr Thr Val
    610                 615                 620

Arg Val Thr Cys Leu Tyr Pro Gly Gly Ser Ser Thr Leu Thr Gly
625                 630                 635                 640

Arg Val Thr Thr Lys Lys Ala Pro Ser Pro Ser Gln Leu Ser Met Thr
                645                 650                 655

Glu Leu Pro Gly Asp Ala Val Gln Leu Ala Trp Val Ala Ala Ala Pro
            660                 665                 670
```

```
Ser Gly Val Leu Val Tyr Gln Ile Thr Trp Thr Pro Leu Gly Glu Gly
        675                 680                 685

Lys Ala His Glu Ile Ser Val Pro Gly Asn Leu Gly Thr Ala Val Leu
        690                 695                 700

Pro Gly Leu Gly Arg His Thr Glu Tyr Asp Val Thr Ile Leu Ala Tyr
705                 710                 715                 720

Tyr Arg Asp Gly Ala Arg Ser Asp Pro Val Ser Leu Arg Tyr Thr Pro
                725                 730                 735

Ser Thr Val Ser Arg Ser Pro Pro Ser Asn Leu Ala Leu Ala Ser Glu
                740                 745                 750

Thr Pro Asp Ser Leu Gln Val Ser Trp Thr Pro Pro Leu Gly Arg Val
                755                 760                 765

Leu His Tyr Trp Leu Thr Tyr Ala Pro Ala Ser Gly Leu Gly Pro Glu
        770                 775                 780

Lys Ser Val Ser Val Pro Gly Ala Arg Ser His Val Thr Leu Pro Asp
785                 790                 795                 800

Leu Gln Ala Ala Thr Lys Tyr Arg Val Leu Val Ser Ala Ile Tyr Ala
                805                 810                 815

Ala Gly Arg Ser Glu Ala Val Ser Ala Thr Gly Gln Thr Ala Cys Pro
                820                 825                 830

Ala Leu Arg Pro Asp Gly Ser Leu Pro Gly Phe Asp Leu Met Val Ala
                835                 840                 845

Phe Ser Leu Val Glu Lys Ala Tyr Ala Ser Ile Arg Gly Val Ala Met
        850                 855                 860

Glu Pro Ser Ala Phe Gly Gly Thr Pro Thr Phe Thr Leu Phe Lys Asp
865                 870                 875                 880

Ala Gln Leu Thr Arg Arg Val Ser Asp Val Tyr Pro Ala Pro Leu Pro
                885                 890                 895

Pro Glu His Thr Ile Val Phe Leu Val Arg Leu Leu Pro Glu Thr Pro
                900                 905                 910

Arg Glu Ala Phe Ala Leu Trp Gln Met Thr Ala Glu Asp Phe Gln Pro
        915                 920                 925

Leu Leu Gly Val Leu Leu Asp Ala Gly Lys Lys Ser Leu Thr Tyr Phe
        930                 935                 940

His Arg Asp Pro Arg Ala Ala Leu Gln Glu Ala Thr Phe Asp Pro Gln
945                 950                 955                 960

Glu Val Arg Lys Ile Phe Phe Gly Ser Phe His Lys Val His Val Ala
                965                 970                 975

Val Gly Arg Ser Lys Val Arg Leu Tyr Val Asp Cys Arg Lys Val Ala
                980                 985                 990

Glu Arg Pro Leu Gly Glu Met Gly Ser Pro Pro Ala Ala Gly Phe Val
        995                 1000                1005

Thr Leu Gly Arg Leu Ala Lys Ala Arg Gly Pro Arg Ser Ser Ser
    1010                1015                1020

Ala Ala Phe Gln Leu Gln Met Leu Gln Ile Val Cys Ser Asp Thr
    1025                1030                1035

Trp Ala Asp Glu Asp Arg Cys Cys Glu Leu Pro Ala Ser Arg Asp
    1040                1045                1050

Gly Glu Thr Cys Pro Ala Phe Val Ser Ala Cys Ser Cys Ser Ser
    1055                1060                1065

Glu Thr Pro Gly Pro Pro Gly Pro Gln Gly Pro Pro Gly Leu Pro
    1070                1075                1080
```

-continued

Gly Arg Asn Gly Thr Pro Gly Glu Gln Gly Phe Pro Gly Pro Arg
    1085                1090                1095

Gly Pro Pro Gly Val Lys Gly Glu Lys Gly Asp His Gly Leu Pro
    1100                1105                1110

Gly Leu Gln Gly His Pro Gly His Gln Gly Ile Pro Gly Arg Val
    1115                1120                1125

Gly Leu Gln Gly Pro Lys Gly Met Arg Gly Leu Glu Gly Thr Ala
    1130                1135                1140

Gly Leu Pro Gly Pro Pro Gly Pro Arg Gly Phe Gln Gly Met Ala
    1145                1150                1155

Gly Ala Arg Gly Thr Ser Gly Glu Arg Gly Pro Pro Gly Thr Val
    1160                1165                1170

Gly Pro Thr Gly Leu Pro Gly Pro Lys Gly Glu Arg Gly Glu Lys
    1175                1180                1185

Gly Glu Pro Gln Ser Leu Ala Thr Leu Tyr Gln Leu Val Ser Gln
    1190                1195                1200

Ala Ser His Val Ser Lys Phe Asp Ser Phe His Glu Asn Thr Arg
    1205                1210                1215

Pro Pro Met Pro Ile Leu Glu Gln Lys Leu Glu Pro Gly Thr Glu
    1220                1225                1230

Pro Leu Gly Ser Pro Gly Thr Arg Ser Lys Ala Leu Val Pro Gly
    1235                1240                1245

Glu Trp Gly Arg Gly Gly Arg His Leu Glu Gly Arg Gly Glu Pro
    1250                1255                1260

Gly Ala Val Gly Gln Met Gly Ser Pro Gly Gln Gln Gly Ala Ser
    1265                1270                1275

Thr Gln Gly Leu Trp Glu
    1280

<210> SEQ ID NO 4
<211> LENGTH: 1111
<212> TYPE: PRT
<213> ORGANISM: Homo sapiens

<400> SEQUENCE: 4

Met Val Phe Leu Val Asp Gly Ser Trp Ser Ile Gly His Ser His Phe
1               5                   10                  15

Gln Gln Val Lys Asp Phe Leu Ala Ser Val Ile Ala Pro Phe Glu Ile
                20                  25                  30

Gly Pro Asp Lys Val Gln Val Gly Leu Thr Gln Tyr Ser Gly Asp Ala
            35                  40                  45

Gln Thr Glu Trp Asp Leu Asn Ser Leu Ser Thr Lys Glu Gln Val Leu
        50                  55                  60

Ala Ala Val Arg Arg Leu Arg Tyr Lys Gly Gly Asn Thr Phe Thr Gly
65                  70                  75                  80

Leu Ala Leu Thr His Val Leu Gly Gln Asn Leu Gln Pro Ala Ala Gly
                85                  90                  95

Leu Arg Pro Glu Ala Ala Lys Val Val Ile Leu Val Thr Asp Gly Lys
            100                 105                 110

Ser Gln Asp Asp Val His Thr Ala Ala Arg Val Leu Lys Asp Leu Gly
        115                 120                 125

Val Asn Val Phe Ala Val Gly Val Lys Asn Ala Asp Glu Ala Glu Leu
    130                 135                 140

Arg Leu Leu Ala Ser Pro Pro Arg Asp Ile Thr Val His Ser Val Leu
145                 150                 155                 160

Asp Phe Leu Gln Leu Gly Ala Leu Ala Gly Leu Leu Ser Arg Leu Ile
              165                 170                 175

Cys Gln Arg Leu Gln Gly Gly Ser Pro Arg Gln Gly Pro Ala Ala Ala
            180                 185                 190

Pro Ala Leu Asp Thr Leu Pro Ala Pro Thr Ser Leu Val Leu Ser Gln
            195                 200                 205

Val Thr Ser Ser Ser Ile Arg Leu Ser Trp Thr Pro Ala Pro Arg His
        210                 215                 220

Pro Leu Lys Tyr Leu Ile Val Trp Arg Ala Ser Arg Gly Gly Thr Pro
225                 230                 235                 240

Arg Glu Val Val Val Glu Gly Pro Ala Ala Ser Thr Glu Leu His Asn
                245                 250                 255

Leu Ala Ser Arg Thr Glu Tyr Leu Val Ser Val Phe Pro Ile Tyr Glu
            260                 265                 270

Gly Gly Val Gly Glu Gly Leu Arg Gly Leu Val Thr Thr Ala Pro Leu
        275                 280                 285

Pro Pro Pro Arg Ala Leu Thr Leu Ala Ala Val Thr Pro Arg Thr Val
290                 295                 300

His Leu Thr Trp Gln Pro Ser Ala Gly Ala Thr His Tyr Leu Val Arg
305                 310                 315                 320

Cys Ser Pro Ala Ser Pro Lys Gly Glu Glu Glu Arg Glu Val Gln
                325                 330                 335

Val Gly Arg Pro Glu Val Leu Leu Asp Gly Leu Glu Pro Gly Arg Asp
            340                 345                 350

Tyr Glu Val Ser Val Gln Ser Leu Arg Gly Pro Glu Gly Ser Glu Ala
            355                 360                 365

Arg Gly Ile Arg Ala Arg Thr Pro Thr Leu Ala Pro Pro Arg His Leu
370                 375                 380

Gly Phe Ser Asp Val Ser His Asp Ala Ala Arg Val Phe Trp Glu Gly
385                 390                 395                 400

Ala Pro Arg Pro Val Arg Leu Val Arg Val Thr Tyr Val Ser Ser Glu
            405                 410                 415

Gly Gly His Ser Gly Gln Thr Glu Ala Pro Gly Asn Ala Thr Ser Ala
            420                 425                 430

Thr Leu Gly Pro Leu Ser Ser Ser Thr Thr Tyr Thr Val Arg Val Thr
            435                 440                 445

Cys Leu Tyr Pro Gly Gly Ser Ser Thr Leu Thr Gly Arg Val Thr
            450                 455                 460

Thr Lys Lys Ala Pro Ser Pro Ser Gln Leu Ser Met Thr Glu Leu Pro
465                 470                 475                 480

Gly Asp Ala Val Gln Leu Ala Trp Val Ala Ala Pro Ser Gly Val
            485                 490                 495

Leu Val Tyr Gln Ile Thr Trp Thr Pro Leu Gly Glu Gly Lys Ala His
                500                 505                 510

Glu Ile Ser Val Pro Gly Asn Leu Gly Thr Ala Val Leu Pro Gly Leu
        515                 520                 525

Gly Arg His Thr Glu Tyr Asp Val Thr Ile Leu Ala Tyr Tyr Arg Asp
        530                 535                 540

Gly Ala Arg Ser Asp Pro Val Ser Leu Arg Tyr Thr Pro Ser Thr Val
545                 550                 555                 560

Ser Arg Ser Pro Pro Ser Asn Leu Ala Leu Ala Ser Glu Thr Pro Asp
                565                 570                 575

```
Ser Leu Gln Val Ser Trp Thr Pro Pro Leu Gly Arg Val Leu His Tyr
            580                 585                 590
Trp Leu Thr Tyr Ala Pro Ala Ser Gly Leu Gly Pro Glu Lys Ser Val
        595                 600                 605
Ser Val Pro Gly Ala Arg Ser His Val Thr Leu Pro Asp Leu Gln Ala
    610                 615                 620
Ala Thr Lys Tyr Arg Val Leu Val Ser Ala Ile Tyr Ala Ala Gly Arg
625                 630                 635                 640
Ser Glu Ala Val Ser Ala Thr Gly Gln Thr Ala Cys Pro Ala Leu Arg
                645                 650                 655
Pro Asp Gly Ser Leu Pro Gly Phe Asp Leu Met Val Ala Phe Ser Leu
            660                 665                 670
Val Glu Lys Ala Tyr Ala Ser Ile Arg Gly Val Ala Met Glu Pro Ser
        675                 680                 685
Ala Phe Gly Gly Thr Pro Thr Phe Thr Leu Phe Lys Asp Ala Gln Leu
    690                 695                 700
Thr Arg Arg Val Ser Asp Val Tyr Pro Ala Pro Leu Pro Pro Glu His
705                 710                 715                 720
Thr Ile Val Phe Leu Val Arg Leu Leu Pro Glu Thr Pro Arg Glu Ala
                725                 730                 735
Phe Ala Leu Trp Gln Met Thr Ala Glu Asp Phe Gln Pro Leu Leu Gly
            740                 745                 750
Val Leu Leu Asp Ala Gly Lys Lys Ser Leu Thr Tyr Phe His Arg Asp
        755                 760                 765
Pro Arg Ala Ala Leu Gln Glu Ala Thr Phe Asp Pro Gln Glu Val Arg
    770                 775                 780
Lys Ile Phe Phe Gly Ser Phe His Lys Val His Val Ala Val Gly Arg
785                 790                 795                 800
Ser Lys Val Arg Leu Tyr Val Asp Cys Arg Lys Val Ala Glu Arg Pro
                805                 810                 815
Leu Gly Glu Met Gly Ser Pro Ala Ala Gly Phe Val Thr Leu Gly
            820                 825                 830
Arg Leu Ala Lys Ala Arg Gly Pro Arg Ser Ser Ser Ala Ala Phe Gln
        835                 840                 845
Leu Gln Met Leu Gln Ile Val Cys Ser Asp Thr Trp Ala Asp Glu Asp
    850                 855                 860
Arg Cys Cys Glu Leu Pro Ala Ser Arg Asp Gly Glu Thr Cys Pro Ala
865                 870                 875                 880
Phe Val Ser Ala Cys Ser Cys Ser Ser Glu Thr Pro Gly Pro Pro Gly
                885                 890                 895
Pro Gln Gly Pro Pro Gly Leu Pro Gly Arg Asn Gly Thr Pro Gly Glu
            900                 905                 910
Gln Gly Phe Pro Gly Pro Arg Gly Pro Pro Gly Val Lys Gly Glu Lys
        915                 920                 925
Gly Asp His Gly Leu Pro Gly Leu Gln Gly His Pro Gly His Gln Gly
    930                 935                 940
Ile Pro Gly Arg Val Gly Leu Gln Gly Pro Lys Gly Met Arg Gly Leu
945                 950                 955                 960
Glu Gly Thr Ala Gly Leu Pro Gly Pro Gly Pro Arg Gly Phe Gln
                965                 970                 975
Gly Met Ala Gly Ala Arg Gly Thr Ser Gly Glu Arg Gly Pro Pro Gly
            980                 985                 990
Thr Val Gly Pro Thr Gly Leu Pro  Gly Pro Lys Gly Glu  Arg Gly Glu
```

-continued

```
                995             1000            1005
Lys Gly Glu Pro Gln Ser Leu Ala Thr Leu Tyr Gln Leu Val Ser
       1010            1015            1020

Gln Ala Cys Glu Ser Ala Ile Gln Thr His Val Ser Lys Phe Asp
       1025            1030            1035

Ser Phe His Glu Asn Thr Arg Pro Pro Met Pro Ile Leu Glu Gln
       1040            1045            1050

Lys Leu Glu Pro Gly Thr Glu Pro Leu Gly Ser Pro Gly Thr Arg
       1055            1060            1065

Ser Lys Ala Leu Val Pro Gly Glu Trp Gly Arg Gly Gly Arg His
       1070            1075            1080

Leu Glu Gly Arg Gly Glu Pro Gly Ala Val Gly Gln Met Gly Ser
       1085            1090            1095

Pro Gly Gln Gln Gly Ala Ser Thr Gln Gly Leu Trp Glu
       1100            1105            1110
```

<210> SEQ ID NO 5
<211> LENGTH: 9
<212> TYPE: PRT
<213> ORGANISM: Homo sapiens

<400> SEQUENCE: 5

```
Ala Leu Ala Gly Leu Leu Ser Arg Leu
1               5
```

<210> SEQ ID NO 6
<211> LENGTH: 9
<212> TYPE: PRT
<213> ORGANISM: Homo sapiens

<400> SEQUENCE: 6

```
Gly Leu Arg Pro Glu Ala Ala Lys Val
1               5
```

<210> SEQ ID NO 7
<211> LENGTH: 9
<212> TYPE: PRT
<213> ORGANISM: Homo sapiens

<400> SEQUENCE: 7

```
Ala Ala Ala Pro Ala Leu Asp Thr Leu
1               5
```

<210> SEQ ID NO 8
<211> LENGTH: 9
<212> TYPE: PRT
<213> ORGANISM: Homo sapiens

<400> SEQUENCE: 8

```
Ser Leu Pro Gly Phe Asp Leu Met Val
1               5
```

<210> SEQ ID NO 9
<211> LENGTH: 9
<212> TYPE: PRT
<213> ORGANISM: Homo sapiens

<400> SEQUENCE: 9

```
Lys Leu Glu Pro Gly Thr Glu Pro Leu
1               5
```

```
<210> SEQ ID NO 10
<211> LENGTH: 9
<212> TYPE: PRT
<213> ORGANISM: Homo sapiens

<400> SEQUENCE: 10

Leu Leu Asp Ala Gly Lys Lys Ser Leu
1               5

<210> SEQ ID NO 11
<211> LENGTH: 9
<212> TYPE: PRT
<213> ORGANISM: Homo sapiens

<400> SEQUENCE: 11

Ser Leu Ala Thr Leu Tyr Gln Leu Val
1               5

<210> SEQ ID NO 12
<211> LENGTH: 9
<212> TYPE: PRT
<213> ORGANISM: Homo sapiens

<400> SEQUENCE: 12

Phe Leu Val Asp Gly Ser Trp Ser Ile
1               5

<210> SEQ ID NO 13
<211> LENGTH: 9
<212> TYPE: PRT
<213> ORGANISM: Homo sapiens

<400> SEQUENCE: 13

Val Leu Lys Asp Leu Gly Val Asn Val
1               5

<210> SEQ ID NO 14
<211> LENGTH: 9
<212> TYPE: PRT
<213> ORGANISM: Homo sapiens

<400> SEQUENCE: 14

Asp Leu Gly Val Asn Val Phe Ala Val
1               5

<210> SEQ ID NO 15
<211> LENGTH: 9
<212> TYPE: PRT
<213> ORGANISM: Homo sapiens

<400> SEQUENCE: 15

Asn Leu Ala Ser Arg Thr Glu Tyr Leu
1               5

<210> SEQ ID NO 16
<211> LENGTH: 9
<212> TYPE: PRT
<213> ORGANISM: Homo sapiens

<400> SEQUENCE: 16

Gly Val Gly Glu Gly Leu Arg Gly Leu
1               5

<210> SEQ ID NO 17
<211> LENGTH: 9
```

<212> TYPE: PRT
<213> ORGANISM: Homo sapiens

<400> SEQUENCE: 17

Gly Leu Arg Gly Leu Val Thr Thr Ala
1               5

<210> SEQ ID NO 18
<211> LENGTH: 9
<212> TYPE: PRT
<213> ORGANISM: Homo sapiens

<400> SEQUENCE: 18

Gly Ile Arg Ala Arg Thr Pro Thr Leu
1               5

<210> SEQ ID NO 19
<211> LENGTH: 9
<212> TYPE: PRT
<213> ORGANISM: Homo sapiens

<400> SEQUENCE: 19

Ser Gly Leu Gly Tyr Leu Val Gln Val
1               5

<210> SEQ ID NO 20
<211> LENGTH: 9
<212> TYPE: PRT
<213> ORGANISM: Homo sapiens

<400> SEQUENCE: 20

Phe Leu Leu Ala Arg Arg Glu Phe Val
1               5

<210> SEQ ID NO 21
<211> LENGTH: 9
<212> TYPE: PRT
<213> ORGANISM: Homo sapiens

<400> SEQUENCE: 21

Gln Val Lys Asp Phe Leu Ala Ser Val
1               5

<210> SEQ ID NO 22
<211> LENGTH: 9
<212> TYPE: PRT
<213> ORGANISM: Homo sapiens

<400> SEQUENCE: 22

Ser Leu Ser Thr Lys Glu Gln Val Leu
1               5

<210> SEQ ID NO 23
<211> LENGTH: 9
<212> TYPE: PRT
<213> ORGANISM: Homo sapiens

<400> SEQUENCE: 23

Leu Leu Ala Ser Pro Pro Arg Asp Ile
1               5

<210> SEQ ID NO 24
<211> LENGTH: 9
<212> TYPE: PRT
<213> ORGANISM: Homo sapiens

<400> SEQUENCE: 24

Leu Gln Leu Gly Ala Leu Ala Gly Leu
1               5

<210> SEQ ID NO 25
<211> LENGTH: 9
<212> TYPE: PRT
<213> ORGANISM: Homo sapiens

<400> SEQUENCE: 25

Thr Leu Pro Ala Pro Thr Ser Leu Val
1               5

<210> SEQ ID NO 26
<211> LENGTH: 9
<212> TYPE: PRT
<213> ORGANISM: Homo sapiens

<400> SEQUENCE: 26

Ser Leu Arg Tyr Thr Pro Ser Thr Val
1               5

<210> SEQ ID NO 27
<211> LENGTH: 9
<212> TYPE: PRT
<213> ORGANISM: Homo sapiens

<400> SEQUENCE: 27

Gln Leu Thr Arg Arg Val Ser Asp Val
1               5

<210> SEQ ID NO 28
<211> LENGTH: 9
<212> TYPE: PRT
<213> ORGANISM: Homo sapiens

<400> SEQUENCE: 28

His Thr Ile Val Phe Leu Val Arg Leu
1               5

<210> SEQ ID NO 29
<211> LENGTH: 9
<212> TYPE: PRT
<213> ORGANISM: Homo sapiens

<400> SEQUENCE: 29

Phe Leu Val Arg Leu Leu Pro Glu Thr
1               5

<210> SEQ ID NO 30
<211> LENGTH: 9
<212> TYPE: PRT
<213> ORGANISM: Homo sapiens

<400> SEQUENCE: 30

Arg Leu Tyr Val Asp Cys Arg Lys Val
1               5

<210> SEQ ID NO 31
<211> LENGTH: 9
<212> TYPE: PRT
<213> ORGANISM: Homo sapiens

<400> SEQUENCE: 31

Leu Leu Ala Arg Arg Glu Phe Val Ile
1               5

<210> SEQ ID NO 32
<211> LENGTH: 9
<212> TYPE: PRT
<213> ORGANISM: Homo sapiens

<400> SEQUENCE: 32

Ser Arg Thr Glu Tyr Leu Val Ser Val
1               5

<210> SEQ ID NO 33
<211> LENGTH: 9
<212> TYPE: PRT
<213> ORGANISM: Homo sapiens

<400> SEQUENCE: 33

Ala Ala Ala Pro Ser Gly Val Leu Val
1               5

<210> SEQ ID NO 34
<211> LENGTH: 9
<212> TYPE: PRT
<213> ORGANISM: Homo sapiens

<400> SEQUENCE: 34

Thr Ile Val Phe Leu Val Arg Leu Leu
1               5

<210> SEQ ID NO 35
<211> LENGTH: 9
<212> TYPE: PRT
<213> ORGANISM: Homo sapiens

<400> SEQUENCE: 35

Ile Leu Thr Thr Lys Thr Pro Lys Ala
1               5

<210> SEQ ID NO 36
<211> LENGTH: 9
<212> TYPE: PRT
<213> ORGANISM: Homo sapiens

<400> SEQUENCE: 36

Gln Leu Gly Ala Leu Ala Gly Leu Leu
1               5

<210> SEQ ID NO 37
<211> LENGTH: 9
<212> TYPE: PRT
<213> ORGANISM: Homo sapiens

<400> SEQUENCE: 37

Ala Ala Ser Thr Glu Leu His Asn Leu
1               5

<210> SEQ ID NO 38
<211> LENGTH: 9
<212> TYPE: PRT
<213> ORGANISM: Homo sapiens

<400> SEQUENCE: 38

Ala Val Thr Pro Arg Thr Val His Leu

```
1               5

<210> SEQ ID NO 39
<211> LENGTH: 9
<212> TYPE: PRT
<213> ORGANISM: Homo sapiens

<400> SEQUENCE: 39

Glu Leu Pro Gly Asp Ala Val Gln Leu
1               5

<210> SEQ ID NO 40
<211> LENGTH: 9
<212> TYPE: PRT
<213> ORGANISM: Homo sapiens

<400> SEQUENCE: 40

Val Leu Val Ser Ala Ile Tyr Ala Ala
1               5

<210> SEQ ID NO 41
<211> LENGTH: 9
<212> TYPE: PRT
<213> ORGANISM: Homo sapiens

<400> SEQUENCE: 41

Tyr Ala Ala Gly Arg Ser Glu Ala Val
1               5

<210> SEQ ID NO 42
<211> LENGTH: 9
<212> TYPE: PRT
<213> ORGANISM: Homo sapiens

<400> SEQUENCE: 42

Lys Ala Tyr Ala Ser Ile Arg Gly Val
1               5

<210> SEQ ID NO 43
<211> LENGTH: 9
<212> TYPE: PRT
<213> ORGANISM: Homo sapiens

<400> SEQUENCE: 43

Val Thr Leu Gly Arg Leu Ala Lys Ala
1               5

<210> SEQ ID NO 44
<211> LENGTH: 9
<212> TYPE: PRT
<213> ORGANISM: Homo sapiens

<400> SEQUENCE: 44

Ser Ala Ala Phe Gln Leu Gln Met Leu
1               5

<210> SEQ ID NO 45
<211> LENGTH: 9
<212> TYPE: PRT
<213> ORGANISM: Homo sapiens

<400> SEQUENCE: 45

Arg Gly Leu Glu Gly Thr Ala Gly Leu
1               5
```

```
<210> SEQ ID NO 46
<211> LENGTH: 9
<212> TYPE: PRT
<213> ORGANISM: Homo sapiens

<400> SEQUENCE: 46

Cys Leu Trp Leu Trp Leu Gly Ala Thr
1               5

<210> SEQ ID NO 47
<211> LENGTH: 9
<212> TYPE: PRT
<213> ORGANISM: Homo sapiens

<400> SEQUENCE: 47

Val Gln Ala Ser Gly Leu Leu Arg Leu
1               5

<210> SEQ ID NO 48
<211> LENGTH: 9
<212> TYPE: PRT
<213> ORGANISM: Homo sapiens

<400> SEQUENCE: 48

Ser Gly Leu Leu Arg Leu Ala Val Leu
1               5

<210> SEQ ID NO 49
<211> LENGTH: 9
<212> TYPE: PRT
<213> ORGANISM: Homo sapiens

<400> SEQUENCE: 49

Gln Thr Glu Trp Asp Leu Asn Ser Leu
1               5

<210> SEQ ID NO 50
<211> LENGTH: 9
<212> TYPE: PRT
<213> ORGANISM: Homo sapiens

<400> SEQUENCE: 50

Gln Val Leu Ala Ala Val Arg Arg Leu
1               5

<210> SEQ ID NO 51
<211> LENGTH: 9
<212> TYPE: PRT
<213> ORGANISM: Homo sapiens

<400> SEQUENCE: 51

Gly Val Asn Val Phe Ala Val Gly Val
1               5

<210> SEQ ID NO 52
<211> LENGTH: 9
<212> TYPE: PRT
<213> ORGANISM: Homo sapiens

<400> SEQUENCE: 52

Leu Ala Ala Val Thr Pro Arg Thr Val
1               5

<210> SEQ ID NO 53
```

```
<211> LENGTH: 9
<212> TYPE: PRT
<213> ORGANISM: Homo sapiens

<400> SEQUENCE: 53

Val Leu Leu Asp Gly Leu Glu Pro Gly
1               5

<210> SEQ ID NO 54
<211> LENGTH: 9
<212> TYPE: PRT
<213> ORGANISM: Homo sapiens

<400> SEQUENCE: 54

Gly Ala Pro Arg Pro Val Arg Leu Val
1               5

<210> SEQ ID NO 55
<211> LENGTH: 9
<212> TYPE: PRT
<213> ORGANISM: Homo sapiens

<400> SEQUENCE: 55

Ala Thr Ser Ala Thr Leu Gly Pro Leu
1               5

<210> SEQ ID NO 56
<211> LENGTH: 9
<212> TYPE: PRT
<213> ORGANISM: Homo sapiens

<400> SEQUENCE: 56

Leu Ala Ser Glu Thr Pro Asp Ser Leu
1               5

<210> SEQ ID NO 57
<211> LENGTH: 9
<212> TYPE: PRT
<213> ORGANISM: Homo sapiens

<400> SEQUENCE: 57

Asp Leu Met Val Ala Phe Ser Leu Val
1               5

<210> SEQ ID NO 58
<211> LENGTH: 9
<212> TYPE: PRT
<213> ORGANISM: Homo sapiens

<400> SEQUENCE: 58

Leu Leu Pro Glu Thr Pro Arg Glu Ala
1               5

<210> SEQ ID NO 59
<211> LENGTH: 9
<212> TYPE: PRT
<213> ORGANISM: Homo sapiens

<400> SEQUENCE: 59
```

```
Pro Leu Leu Gly Val Leu Leu Asp Ala
1               5

<210> SEQ ID NO 60
<211> LENGTH: 9
<212> TYPE: PRT
<213> ORGANISM: Homo sapiens

<400> SEQUENCE: 60

His Val Ala Val Gly Arg Ser Lys Val
1               5

<210> SEQ ID NO 61
<211> LENGTH: 9
<212> TYPE: PRT
<213> ORGANISM: Homo sapiens

<400> SEQUENCE: 61

Thr Leu Tyr Gln Leu Val Ser Gln Ala
1               5

<210> SEQ ID NO 62
<211> LENGTH: 9
<212> TYPE: PRT
<213> ORGANISM: Homo sapiens

<400> SEQUENCE: 62

Gln Leu Val Ser Gln Ala Ser His Val
1               5

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide

<400> SEQUENCE: 63
ttcacgctct tcaaggacgc                                           20

<210> SEQ ID NO 64
<211> LENGTH: 20
<212> TYPE: DNA
<213> ORGANISM: Artificial Sequence
<220> FEATURE:
<223> OTHER INFORMATION: Oligonucleotide

<400> SEQUENCE: 64
tggaagtcct cggctgtcat                                           20
```

METHODS AND COMPOSITIONS FOR DIAGNOSIS AND TREATMENT OF CANCER

TECHNICAL FIELD OF THE INVENTION

The present invention relates to the treatment and diagnosis of cancerous diseases, in particular cancerous diseases of the central nervous system, such as glioma. More particularly, the invention concerns novel targets for cancer treatment, in particular their use as tumor antigens for immune therapy.

BACKGROUND OF THE INVENTION

Glioblastoma multiforme (GBM) is the most common and lethal primary malignancy of the central nervous system (CNS), with an annual incidence of ~190.000 new cases.

GBM are tumors of the neuroepithelial tissue, attributed to the group of astrocytic tumors and classified by the World Health Organization (WHO) as a grade IV glioma. The designation WHO grade IV is assigned to cytologically malignant, mitotically active, necrosis-prone neoplasms typically associated with rapid pre- and postoperative disease evolution and a fatal outcome.

The current standard of care for patients with GBM includes surgical resection, followed by a combination of radiation therapy (RT) to the resection cavity and chemotherapy with temozolomide (TMZ) and a consecutive treatment with several adjuvant cycles of TMZ.

Surgical resection alone results in a median survival of approximately 6 months. Combined, surgical resection and RT extend median survival to 12.1 months. Addition of TMZ further extends the median survival to 14.6 months.

Beside the proven benefit of surgical resection and aggressive treatment with chemo- and radiotherapy, the prognosis remains very poor. As an alternative modality of treatment novel therapeutic approaches were developed including targeted therapies, immunotherapies and gene therapy.

Immunotherapy is one of the most elegant concepts in cancer therapy. The central idea is based on recruiting and restoring reactivity of the host's immune system to combat cancer. Several immotherapeutical approaches have been successfully introduced into the clinic and have emerged as the most promising therapeutics in oncology. The limiting factor regarding the development of therapeutical vaccines is the identification of tumor-associated antigens.

Tumor cells biologically differ substantially from their nonmalignant cells of origin. These differences are due to genetic alterations acquired during tumor development and result, inter alia, also in the formation of qualitatively or quantitatively altered molecular structures in the cancer cells. Furthermore tumor cells may also induce surrounding stroma cells to propagate cancer progression by regulating local cytokine levels, which results in altered molecular structures in these genetically unchanged stroma cells differing from non cancerous tissues. Tumor associated structures of this kind, which are recognized by the specific immune system of the tumor-harboring host, are referred to as tumor-associated antigens. The specific recognition of tumor-associated antigens involves cellular and humoral mechanisms which are two functionally interconnected units: CD4+ and CD8+T-lymphocytes recognize the processed antigens presented on the molecules of the MHC (major histocompatibility complex) classes II and I, respectively, while B lymphocytes produce circulating antibody molecules which bind directly to unprocessed antigens. The potential clinical-therapeutical importance of tumor-associated antigens results from the fact that the recognition of antigens on neoplastic cells by the immune system leads to the initiation of cytotoxic effector mechanisms and, in the presence of T helper cells, can cause elimination of the cancer cells (Pardoll, Nat. Med. 4:525-31, of the 1998).

There is a need in the art for genetic markers and targets of tumors of the central nervous system (CNS) such as glioma, in particular glioblastoma, allowing the design of specific, reliable and sensitive diagnostic and therapeutic approaches of these diseases.

The invention relates to the therapy and diagnosis of tumors of the central nervous system such as glioma, in particular glioblastoma. In particular, the invention relates to the identification of molecular structures that are associated with tumors of the central nervous system such as glioma, in particular glioblastoma, and can serve as targets for diagnostic and therapeutic approaches of these diseases.

SUMMARY OF THE INVENTION

The present invention relates to the identification of nucleic acid and amino acid sequences that are characteristic of tumor tissues of tumors of the central nervous system such as glioma, in particular glioblastoma, and which represent targets for therapy or diagnosis of tumors of the central nervous system such as glioma, in particular glioblastoma in a subject.

The nucleic acids identified according to the invention to be expressed in association with tumor cells comprise the nucleic acid sequence according to SEQ ID NO: 1 or 2 of the sequence listing or a variant of said nucleic acid sequence. Preferably, the nucleic acids identified according to the invention to be expressed in association with tumor cells encode a peptide comprising the amino acid sequence according to SEQ ID NO: 3 or 4 of the sequence listing or a variant of said amino acid sequence. These nucleic acids are also termed "tumor-associated nucleic acids" or simply "tumor nucleic acids" herein.

In another aspect, the invention relates to peptides encoded by the tumor nucleic acids identified according to the invention, also termed "tumor-associated antigens" or simply "tumor antigens" herein. Accordingly, the tumor antigens identified according to the invention comprise an amino acid sequence encoded by a nucleic acid which comprises the nucleic acid sequence according to SEQ ID NO: 1 or 2 of the sequence listing or a variant of said nucleic acid sequence. Preferably, the tumor antigens identified according to the invention comprise the amino acid sequence according to SEQ ID NO: 3 or 4 of the sequence listing or a variant of said amino acid sequence.

In one aspect, the invention provides peptides comprising amino acid sequences derived from the sequences of the tumor antigens identified according to the invention, also termed "tumor antigen peptides" herein. Preferably, the tumor antigen peptides of the invention are capable of stimulating a cellular response against cells characterized by presentation of a tumor antigen identified according to the invention with class I MHC and/or of eliciting antibodies that specifically bind to a tumor antigen identified according to the invention when used itself or attached to an immunogenic carrier. Preferred tumor antigen peptides may be presented, directly or following processing, with class I MHC molecules. Preferably, the tumor antigen peptides according to the invention are MHC class I and/or class II presented peptides or can be processed to produce MHC class I and/or class II presented peptides. Preferably, the tumor antigen peptides according to the invention comprise an amino acid sequence substantially corresponding to the amino acid sequence of a fragment of a tumor antigen identified according to the invention. Preferably, said fragment of a tumor antigen identified according to the invention is a MHC class I and/or class II presented peptide or is an immunogen that is capable of eliciting antibodies binding to said fragment. Preferably, a tumor antigen peptide according to the invention comprises an amino acid sequence substantially corresponding to the amino acid sequence of such fragment and is processed to produce such fragment, i.e. a MHC class I and/or class II presented peptide derived from a tumor antigen identified according to the invention or an immunogen derived from a tumor antigen identified according to the invention that is capable of eliciting antibodies binding to said fragment. Thus, a tumor antigen peptide according to the invention comprises an amino acid sequence substantially corresponding to the amino acid sequence of a fragment of a tumor antigen comprising an amino acid sequence encoded by a nucleic acid which comprises the nucleic acid sequence according to SEQ ID NO: 1 or 2 of the sequence listing or a variant of said nucleic acid sequence and preferably comprises an amino acid sequence substantially corresponding to the amino acid sequence of a fragment of a tumor antigen comprising the amino acid sequence according to SEQ ID NO: 3 or 4 of the sequence listing or a variant of said amino acid sequence. In one embodiment, a tumor antigen peptide according to the invention comprises an amino acid sequence selected from the group consisting of SEQ ID NOs: 5 to 62 of the sequence listing, or a variant of said amino acid sequence.

The present invention generally embraces the treatment and/or diagnosis of tumor diseases of the central nervous system such as glioma, in particular glioblastoma by targeting tumor nucleic acids or tumor antigens. These methods provide for the selective detection of cells and/or eradication of cells that are associated with such tumor nucleic acids and/or tumor antigens thereby minimizing adverse effects to normal cells not being associated with such tumor nucleic acids and/or tumor antigens. Thus, preferred diseases for a therapy or diagnosis are those in which one or more of the tumor nucleic acids and/or tumor antigens identified according to the invention are associated with tumors of the central nervous system such as glioma, in particular glioblastoma.

One aspect of this invention relates to therapies for treatment of tumor diseases, in particular tumors of the central nervous system such as glioma, in particular glioblastoma, involving the administration of an inhibitor of expression and/or activity of a tumor antigen identified according to the invention.

In this aspect, the present invention relates to a pharmaceutical composition comprising an inhibitor of expression and/or activity of a tumor antigen identified according to the invention. In one embodiment, said inhibitor is specific for a tumor nucleic acid identified according to the invention. In another embodiment, said inhibitor is specific for a tumor antigen identified according to the invention. According to the invention the phrase "inhibit expression and/or activity" includes a complete or essentially complete inhibition of expression and/or activity and a reduction in expression and/or activity. Preferably, said inhibition of expression of a tumor antigen identified according to the invention may take place by inhibiting the production of or reducing the level of transcript, i.e. mRNA, coding for a tumor antigen identified according to the invention, e.g. by inhibiting transcription or inducing degradation of transcript, and/or by inhibiting the production of tumor antigen identified according to the invention, e.g. by inhibiting translation of transcript coding for a tumor antigen identified according to the invention. Preferably, said inhibition of expression and/or activity of a tumor antigen identified according to the present invention reduces tumor cell growth and/or induces tumor cell death and thus, has a tumor-inhibiting or tumor-destroying effect.

In a particular embodiment, the inhibitor of expression of a tumor antigen identified according to the invention is an inhibitory nucleic acid (e.g., anti-sense oligonucleotide, ribozyme, iRNA, siRNA or a DNA encoding the same) selectively hybridizing to and being specific for a tumor nucleic acid identified according to the invention, thereby inhibiting (e.g., reducing) transcription and/or translation thereof.

Inhibitory nucleic acids of this invention include oligonucleotides having sequences in the antisense orientation relative to the target nucleic acids. Suitable inhibitory oligonucleotides typically vary in length from five to several hundred nucleotides, more typically about 20-70 nucleotides in length or shorter, even more typically about 10-30 nucleotides in length. These inhibitory oligonucleotides may be administered as free (naked) nucleic acids or in protected forms, e.g., encapsulated in liposomes. The use of liposomal or other protected forms may be advantageous as it may enhance in vivo stability and thus facilitate delivery to target sites.

Also, the target tumor nucleic acid may be used to design ribozymes that target the cleavage of the corresponding mRNAs. Similarly, these ribozymes may be administered in free (naked) form or by the use of delivery systems that enhance stability and/or targeting, e.g., liposomes.

Also, the target tumor nucleic acid may be used to design siRNAs that can inhibit (e.g., reduce) expression of the tumor nucleic acid. The siRNAs may be administered in free (naked) form or by the use of delivery systems that enhance stability and/or targeting, e.g., liposomes. They may also be administered in the form of their precursors or encoding DNAs.

siRNA preferably comprises a sense RNA strand and an antisense RNA strand, wherein the sense and antisense RNA strands form an RNA duplex, and wherein the sense RNA strand comprises a nucleotide sequence substantially identical to a target sequence of about 19 to about 25 contiguous nucleotides in a tumor nucleic acid identified according to the invention, preferably mRNA coding for the target tumor antigen.

In a further embodiment, the inhibitor of activity of a tumor antigen identified according to the invention is an antibody that specifically binds to said tumor antigen. Binding of the antibody to the tumor antigen can interfere with the function of the tumor antigen, e.g. by inhibiting binding activity or catalytic activity.

Also, the present invention in another aspect relates to therapies for treatment of tumor diseases, in particular tumors of the central nervous system such as glioma, in particular glioblastoma, involving the administration of a ligand of a target molecule, i.e. a tumor nucleic acid or tumor antigen identified according to the invention. In this respect, a nucleic acid may be administered that selectively hybridizes to the target nucleic acid or an antibody may be administered that specifically binds to a target antigen, attached to therapeutic effector moieties, e.g., radiolabels, cytotoxins, cytotoxic enzymes, and the like in order to selectively target and kill cells that express these targets, e.g. tumor cells.

In this aspect, the present invention relates to a pharmaceutical composition, comprising a ligand of a tumor nucleic acid or tumor antigen identified according to the invention, said ligand being attached to one or more therapeutic effector moieties. Preferably, said ligand is specific for said tumor nucleic acid or tumor antigen. In one embodiment, said ligand of a tumor nucleic acid or tumor antigen reduces tumor cell growth and/or induces tumor cell death and thus, has a tumor-inhibiting or tumor-destroying effect.

According to a further aspect of the invention, the identification of tumor nucleic acids and tumor antigens makes it possible to develop specific immunotherapies based on attacking tumor cells associated with the identified antigens, thereby delaying or preventing the development of a tumor disease or eradicating tumor cells. Immunotherapy encompasses a variety of interventions and techniques with the common goal of eliciting tumor cell destructive immune responses. A variety of clinical approaches utilising these nucleic acids and antigens are possible as summarised below. Approaches to cancer immunotherapy can be divided into active and passive categories. Active immunotherapy may involve the direct immunization of patients with antigens or nucleic acids encoding such antigens in an attempt to boost immune responses against the tumor. Passive immunotherapy refers to the administration of immune reagents with the goal of directly mediating antitumor responses. The present invention contemplates both approaches.

In this aspect, the invention relates to a pharmaceutical composition which comprises one or more agents selected from the group consisting of (i) a peptide comprising the amino acid sequence of a tumor antigen identified according to the invention or of a tumor antigen peptide derived from said tumor antigen, or a derivative of said peptide, (ii) a nucleic acid which codes for a peptide comprising the amino acid sequence of a tumor antigen identified according to the invention or of a tumor antigen peptide derived from said tumor antigen, or a derivative of said nucleic acid, (iii) a host cell which codes for a peptide comprising the amino acid sequence of a tumor antigen identified according to the invention or of a tumor antigen peptide derived from said tumor antigen, (iv) a virus which codes for a peptide comprising the amino acid sequence of a tumor antigen identified according to the invention or of a tumor antigen peptide derived from said tumor antigen, (v) a cell presenting a peptide comprising the amino acid sequence of a tumor antigen peptide derived from a tumor antigen identified according to the invention, or a derivative of said peptide, (vi) an antibody or T cell receptor which binds to a peptide comprising the amino acid sequence of a tumor antigen identified according to the invention or of a tumor antigen peptide derived from said tumor antigen, (vii) an immuno-reactive cell sensitized in vitro to recognize a peptide comprising the amino acid sequence of a tumor antigen identified according to the invention or of a tumor antigen peptide derived from said tumor antigen, and (viii) an effector cell (or stem cell) transduced with a nucleic acid encoding a T cell receptor that recognises a peptide comprising the amino acid sequence of a tumor antigen identified according to the invention or of a tumor antigen peptide derived from said tumor antigen.

In one embodiment, a peptide according to (i) is a tumor antigen specific MHC class I or class II presented peptide or can be processed to produce a tumor antigen specific MHC class I or class II presented peptide, preferably a tumor antigen specific MHC class I presented peptide. Preferably, said peptide has a sequence substantially corresponding to a fragment of a tumor antigen identified according to the invention which is presented by MHC class I or class II, preferably MHC class I or can be processed to produce a peptide fragment having such sequence. Preferably, said peptide is capable of stimulating a cellular response against a tumor characterized by presentation of a tumor antigen identified according to the invention with class I MHC and/or is capable of stimulating a humoral immune response against a tumor characterized by expression of a tumor antigen identified according to the invention. In one embodiment, said peptide comprises an amino acid sequence selected from the group consisting of SEQ ID NOs: 5 to 62 of the sequence listing, or a variant of said amino acid sequence.

In one embodiment, a nucleic acid according to (ii) codes for a tumor antigen specific MHC class I or class II presented peptide or codes for a peptide which can be processed to produce a tumor antigen specific MHC class I or class II presented peptide, preferably a tumor antigen specific MHC class I presented peptide. Preferably, said peptide has a sequence substantially corresponding to a fragment of a tumor antigen identified according to the invention which is presented by MHC class I or class II, preferably MHC class I or can be processed to produce a peptide fragment having such sequence. Preferably, said peptide is capable of stimulating a cellular response against a tumor characterized by presentation of a tumor antigen identified according to the invention with class I MHC and/or is capable of stimulating a humoral immune response against a tumor characterized by expression of a tumor antigen identified according to the invention. In one embodiment, said peptide comprises an amino acid sequence selected from the group consisting of SEQ ID NOs: 5 to 62 of the sequence listing, or a variant of said amino acid sequence. Such nucleic acid may be present in a plasmid or an expression vector and may be functionally linked to a promoter.

In one embodiment, a host cell according to (iii) codes for a tumor antigen specific MHC class I or class II presented peptide or codes for a peptide which can be processed to produce a tumor antigen specific MHC class I or class II presented peptide, preferably a tumor antigen specific MHC class I presented peptide. Preferably, said peptide has a sequence substantially corresponding to a fragment of a tumor antigen identified according to the invention which is presented by MHC class I or class II, preferably MHC class I or can be processed to produce a peptide fragment having such sequence. Preferably, said peptide is capable of stimulating a cellular response against a tumor characterized by presentation of a tumor antigen identified according to the invention with class I MHC and/or is capable of stimulating a humoral immune response against a tumor characterized by expression of a tumor antigen identified according to the invention. In one embodiment, said peptide comprises an amino acid sequence selected from the group consisting of SEQ ID NOs: 5 to 62 of the sequence listing, or a variant of said amino acid sequence. The host cell may be a recombinant cell and may secrete the encoded peptide or a procession product thereof, may express it on the surface and preferably may additionally express an MHC molecule which binds to said peptide or a procession product thereof and preferably presents said peptide or a procession product thereof on the cell surface. In one embodiment, the host cell expresses the MHC molecule endogenously. In a further embodiment, the host cell expresses the MHC molecule and/or the peptide or the procession product thereof in a recombinant manner. The host cell is preferably nonproliferative. In a preferred embodiment, the host cell is an antigen-presenting cell, in particular a dendritic cell, a monocyte or a macrophage.

In one embodiment, a virus according to (iv) codes for a tumor antigen specific MHC class I or class II presented peptide or codes for a peptide which can be processed to produce a tumor antigen specific MHC class I or class II presented peptide, preferably a tumor antigen specific MHC class I presented peptide. Preferably, said peptide has a sequence substantially corresponding to a fragment of a tumor antigen identified according to the invention which is presented by MHC class I or class II, preferably MHC class I or can be processed to produce a peptide fragment having such sequence. Preferably, said peptide is capable of stimulating a cellular response against a tumor characterized by presentation of a tumor antigen identified according to the invention with class I MHC and/or is capable of stimulating a humoral immune response against a tumor characterized by expression of a tumor antigen identified according to the invention. In one embodiment, said peptide comprises an amino acid sequence selected from the group consisting of SEQ ID NOs: 5 to 62 of the sequence listing, or a variant of said amino acid sequence.

In one embodiment, a cell according to (v) endogenously expresses an MHC molecule. In a further embodiment, the cell recombinantly expresses an MHC molecule and/or a peptide comprising the amino acid sequence of a tumor antigen peptide derived from a tumor antigen identified according to the invention. Preferably, the cell presents the peptide comprising the amino acid sequence of a tumor antigen peptide derived from a tumor antigen identified according to the invention, or a derivative of said peptide by MHC molecules on its surface. Preferably, the presented peptide is a peptide having a sequence substantially corresponding to a fragment of a tumor antigen identified according to the invention which is presented by MHC class I or class II, preferably MHC class I. The cell is preferably nonproliferative. In a preferred embodiment, the cell is an antigen-presenting cell such as a dendritic cell, a monocyte or a macrophage. Thus, in a preferred embodiment, the cell according to (v) is an antigen presenting cell that comprises a tumor antigen peptide as described herein presented with class I MHC.

In one embodiment, an antibody according to (vi) is a monoclonal antibody. In further embodiments, the antibody is a chimeric, human or humanized antibody, or is a fragment of an antibody or a synthetic antibody. The antibody may be coupled to a therapeutic effector moiety or a detectable label. Preferably, the antibody or T cell receptor according to (vi) binds to a sequence in the peptide substantially corresponding to a fragment of a tumor antigen identified according to the invention. In one embodiment, said antibody or T cell receptor binds to a peptide comprises an amino acid sequence selected from the group consisting of SEQ ID NOs: 5 to 62 of the sequence listing, or a variant of said amino acid sequence.

Preferably, a cell according to (vii) binds to a sequence in the peptide substantially corresponding to a fragment of a tumor antigen identified according to the invention which fragment is preferably presented by MHC class I or class II, preferably MHC class I. In one embodiment, a cell according to (vii) is obtainable by a method comprising the steps of (a) providing a sample containing immunoreactive cells, either obtained from a patient or from another individual of the same species, in particular a healthy individual, or an individual of a different species, (b) contacting said sample with cells presenting a peptide comprising an amino acid sequence substantially corresponding to a fragment of a tumor antigen identified according to the invention, or a derivative of said peptide, under conditions which favor production of CTLs against said peptide, and (c) introducing the CTLs into the patient in an amount suitable for lysing cells expressing the tumor antigen and preferably presenting it with class I MHC such as tumor cells.

In one embodiment, the method includes cloning of the T cell receptor of CTLs obtained and transferring the nucleic acid coding for the T cell receptor to effector cells such as CTLs or immature CTLs, either obtained from said patient or from another individual of the same species, in particular a healthy individual, or an individual of a different species, which effector cells thus receive the desired specificity and may be introduced into the patient. Effector cells according to (viii) can be produced in this way.

Vaccination using agents as described above may provide MEW class II-presented epitopes that are capable of eliciting a CD4+ helper T-cell response and/or a CD8+ T-cell response against tumor antigens identified according to the invention, in particular if expressed in cells such as tumor cells. Alternatively or additionally, vaccination using agents as described above may provide MHC class I-presented epitopes that are capable of eliciting a CD8+ T-cell response against tumor antigens identified according to the invention, in particular if expressed in cells such as tumor cells. Furthermore, vaccination using agents as described above may elicit antibodies specific for a tumor antigen identified according to the invention.

In one embodiment, the pharmaceutical composition of the present invention is a therapeutic or prophylactic anti-tumor vaccine preferably further comprising an immunomodulatory agent, or a nucleic acid encoding the same. In one embodiment, the immunomodulatory agent is an agonist of a positive costimulatory molecule, e.g., an Ig-fusion protein capable of effecting costimulation of a CTL. In another embodiment, the costimulatory agent is an antagonist of a negative costimulatory molecule, e.g., an antibody capable of reducing inhibition of CTL costimulation. In a preferred embodiment, the immunomodulatory agent is an anti-CTLA4 antibody.

A pharmaceutical composition of the invention may comprise a pharmaceutically acceptable carrier and may optionally comprise one or more adjuvants, stabilizers etc.

Another aspect of the invention involves the use of the agents and compositions described herein for a prophylactic and/or therapeutic treatment of tumor diseases, in particular tumors of the central nervous system such as glioma, in particular glioblastoma.

In one aspect, the invention provides therapeutic and prophylactic methods of treating a patient having a tumor disease or being at risk of developing a tumor disease. In one aspect, the invention provides methods for inhibiting tumor growth. In one aspect, the invention provides methods for inducing tumor cell death.

Preferably, the tumor disease is a tumor disease of the central nervous system such as glioma, in particular glioblastoma. Preferably, the tumor disease is a cancer disease, preferably selected from the group consisting of cancer of the central nervous system such as glioma, in particular glioblastoma.

According to various embodiments, the methods of the invention comprise the administration of an inhibitor of expression and/or activity of a tumor antigen identified according to the invention, of a ligand of a tumor nucleic acid or of a tumor antigen identified according to the invention and/or of one or more immunotherapeutic agents as described herein. In one embodiment, the methods involve administering a pharmaceutical composition as described herein to a patient and preferably vaccinating a patient with an anti-tumor vaccine described herein. Any of the wide variety of vaccination methods known in the art may be used according to the present invention. Anti-tumor vaccines of the invention are preferably capable of inducing or promoting CTL activity against a tumor characterized by presentation of a tumor antigen identified according to the invention with class I MHC. These may be used in combination with adjuvants, which facilitate stimulation of the immune system by acting on T cells directly or through APCs. Adjuvants include immunomodulatory substances having a positive immunomodulatory effect, as described herein.

In various embodiment, the methods of the invention involve the stimulation of an anti-tumor CTL response against a tumor, in particular tumor cells, associated with a tumor antigen identified according to the invention and preferably presenting a tumor antigen identified according to the invention with class I MHC, the inhibition of the growth of a tumor, in particular tumor cells, associated with a tumor antigen identified according to the invention and preferably presenting a tumor antigen identified according to the invention with class I MHC, and/or the induction of the death of a tumor, in particular tumor cells, associated with a tumor antigen identified according to the invention and preferably presenting a tumor antigen identified according to the invention with class I MHC.

In one aspect, the invention provides an inhibitor of expression and/or activity of a tumor antigen identified according to the invention, a ligand of a tumor nucleic acid or of a tumor antigen identified according to the invention and/or one or more immunotherapeutic agents as described herein for use in the methods of treatment described herein. In one embodiment, the invention provides a pharmaceutical composition as described herein for use in the methods of treatment described herein.

The treatments based on targeting tumor nucleic acids or tumor antigens such as the immunotherapies described herein can be combined with surgical resection and/or radiation and/or traditional chemotherapy.

Another object of the invention is to provide methods for diagnosis, detection or monitoring, i.e. determining the regression, progression, course and/or onset, of a tumor disease, in particular a tumor disease of the central nervous system such as glioma, in particular glioblastoma. Preferably said methods involve the use of ligands such as monoclonal antibodies and nucleic acid probes which specifically bind to a target molecule. Suitable target molecules are (i) a tumor nucleic acid identified according to the invention, (ii) a tumor antigen identified according to the invention or a tumor antigen peptide derived therefrom, (iii) an antibody against a tumor antigen identified according to the invention or a tumor antigen peptide derived therefrom, (iv) a T cell which recognizes a tumor antigen identified according to the invention or a tumor antigen peptide derived therefrom and/or (v) a cell which presents a tumor antigen peptide derived from a tumor antigen identified according to the invention with class I or class II MHC, preferably class I MHC. Such methods may be used to detect whether a subject has or is at (increased) risk of developing a tumor disease, in particular a tumor disease of the central nervous system such as glioma, in particular glioblastoma, or, for instance, whether a treatment regimen is efficient.

Accordingly, the present invention relates to methods for diagnosis, detection or monitoring of a tumor disease, in particular a tumor disease of the central nervous system such as glioma, in particular glioblastoma, comprising the detection of and/or determination of the quantity of one or more parameters selected from the group consisting of (i) a nucleic acid which comprising the nucleic acid sequence of a tumor nucleic acid identified according to the invention/a nucleic acid which codes for a peptide comprising the amino acid sequence of a tumor antigen identified according to the invention, (ii) a peptide comprising the amino acid sequence of a tumor antigen identified according to the invention or of a tumor antigen peptide derived from said tumor antigen, (iii) an antibody which binds to a peptide comprising the amino acid sequence of a tumor antigen identified according to the invention or of a tumor antigen peptide derived from said tumor antigen, (iv) a T cell that recognises a peptide comprising the amino acid sequence of a tumor antigen identified according to the invention or of a tumor antigen peptide derived from said tumor antigen and/or (v) a cell which presents a peptide comprising the amino acid sequence of a tumor antigen peptide derived from a tumor antigen identified according to the invention with class I or class II MHC, preferably class I MHC, in a biological sample isolated from a patient, preferably from a patient having a tumor disease, being suspected of having or falling ill with a tumor disease or having a potential for a tumor disease, wherein said tumor disease preferably is a tumor disease of the central nervous system such as glioma, in particular glioblastoma.

In one embodiment, a nucleic acid according to (i) codes for a peptide which is processed to produce a tumor antigen specific MHC class I or class II presented peptide, preferably, a tumor antigen specific MHC class I presented peptide.

In one embodiment, a peptide according to (ii) is a tumor antigen specific MHC class I or class II presented peptide or can be processed to produce a tumor antigen specific MHC class I or class II presented peptide, preferably, a tumor antigen specific MHC class I presented peptide.

Preferably, a T cell according to (iv) recognizes a sequence in the peptide substantially corresponding to a fragment of a tumor antigen identified according to the invention which is presented by MHC class I or class II, preferably MHC class I.

In one embodiment, a cell according to (v) presents the peptide by MHC class I or class II, preferably MHC class I on its surface. The cell is preferably nonproliferative. In a preferred embodiment, the cell is an antigen-presenting cell such as a dendritic cell, a monocyte or a macrophage. Thus, in a preferred embodiment, the cell according to (v) is an antigen presenting cell that comprises a tumor antigen peptide as described herein presented with class I MHC. In another embodiment, the cell is a tumor cell.

In one embodiment, the nucleic acid according to (i) or the peptide according to (ii) is detected or its quantity determined in situ in a cell, preferably a tumor cell. In one embodiment, the peptide according to (ii) is detected or its quantity determined in situ on the surface of a cell in a complex with MHC class I or class II, preferably MHC class I.

Preferably, the tumor disease which is to be diagnosed, detected or monitored using the method of the invention is a tumor disease of the central nervous system such as glioma, in particular glioblastoma. Preferably, the tumor disease is a cancer disease, preferably selected from the group consisting of cancer of the central nervous system such as glioma, in particular glioblastoma In one embodiment of the method for diagnosis, detection or monitoring of a tumor disease according to the invention, a biological sample and/or a control/reference sample is from a tissue or organ corresponding to the tissue or organ which is to be diagnosed, detected or monitored with respect to affection by a tumor disease; e.g. the tumor disease which is to be diagnosed, detected or monitored is brain cancer and the biological sample and/or control/reference sample is brain tissue.

The methods for diagnosis, detection or monitoring allow quantitative and/or qualitative evaluations, e.g., absolute and/or relative measure of target molecules e.g. expression levels of a tumor nucleic acid or a tumor antigen.

Means for accomplishing said detection and/or determination of the quantity are described herein and will be apparent to the skilled person.

Preferably, the detection and/or determination of the quantity in the methods of the invention comprises (i) contacting a biological sample with an agent which binds specifically to the nucleic acid, the peptide, the antibody, the T cell or the cell which is to be detected and/or the amount of which is to be determined, and (ii) detecting the formation of and/or determining the quantity of a complex between the agent and the nucleic acid, the peptide, the antibody, the T cell or the cell which is to be detected or the amount of which is to be determined.

Typically, the level of a target molecule in a biological sample is compared to a reference level, wherein a deviation from said reference level is indicative of the presence and/or stage of a tumor disease in a subject. The reference level may be a level as determined in a control sample (e.g., from a healthy tissue or subject) or a median level from healthy subjects. A "deviation" from said reference level designates any significant change, such as an increase or decrease by at least 10%, 20%, or 30%, preferably by at least 40% or 50%, or even more. Preferably, the presence of the nucleic acid, the peptide, the antibody, the T cell and/or the cell in said biological sample or a quantity of the nucleic acid, the peptide, the antibody, the T cell and/or the cell in the biological sample which is increased compared to a reference level indicates the presence of a tumor disease.

Typically, the detection and/or determination of the quantity in the methods of the invention involves the use of labeled ligands which specifically bind to a target molecule, e.g. a labeled nucleic acid probe that hybridizes to a target nucleic acid and/or a labeled antibody or fragment/derivative thereof that specifically binds to a target peptide.

According to the invention, detection of a nucleic acid or determining the quantity of a nucleic acid may be carried out using known nucleic acid detection methods such as methods involving hybridization or nucleic acid amplification techniques. In one embodiment, mRNA transcripts are detected or the quantity thereof is determined using RT-PCR or Northern blot analysis.

Such nucleic acid detection methods may involve the use of oligonucleotides hybridizing to the target nucleic acids. Suitable oligonucleotides typically vary in length from five to several hundred nucleotides, more typically about 20-70 nucleotides in length or shorter, even more typically about 10-30 nucleotides in length.

According to the invention, detection of a peptide or determining the quantity of a peptide may be carried out in a number of ways, including but not limited to immunodetection using an antibody binding specifically to said peptide. Preferably, the antibody binds to a sequence substantially corresponding to a fragment of a tumor antigen identified according to the invention.

Methods for using antibodies to detect peptides are well known and include ELISA, competitive binding assays, and the like. In general, such assays use an antibody or antibody fragment that specifically binds the target peptide directly or indirectly bound to a label that provides for detection, e.g. indicator enzymes, radiolabels, fluorophores, or paramagnetic particles.

According to the invention, detection of an antibody or determining the quantity of an antibody may be carried out using a peptide binding specifically to said antibody.

T cells may be isolated from patient peripheral blood, lymph nodes, tissue samples such as derived from biopsy and resection, or other source. Reactivity assays may be performed on primary T cells or other appropriate derivatives. For example, T cells may be fused to generate hybridomas. Assays for measuring T cell responsiveness are known in the art, and include proliferation assays and cytokine release assays.

In one embodiment, the T cell that recognises a peptide comprising the amino acid sequence of a tumor antigen identified according to the invention or of a tumor antigen peptide derived from said tumor antigen is a tumor antigen-responsive CTL.

A CTL may be detected and its quantity determined in a number of ways, including but not limited to the following preferred embodiments. In one embodiment, CTLs are directly stained using an appropriate fluorescent tumor antigen peptide/WIC tetramer. In another embodiment, the "TRAP" assay ("T-cell recognition of APCs by protein transfer") is used (see, for example, Beadling et al. Nature Medicine 12:1208 (2006)). In another embodiment, detection of T cells in blood samples is performed using methods outlined by Yuan et al. (Cytotherapy 8:498, 2006). Assays and indices for detecting reactive T cells are known, and include but are not limited to the use of IFN-gamma ELISPOT and IFN-gamma intracellular cytokine staining.

Other various methods are known in the art for determining whether a T cell clone will respond to a particular antigenic peptide. Typically the peptide is added to a suspension of the T cells for a period of from one to three days. The response of the T cells may be measured by proliferation, e.g., uptake of labeled thymidine, or by release of cytokines, e.g., IL-2. Various assays are available for detecting the presence of released cytokines.

T cell cytotoxic assays can be used to detect cytotoxic T cells having specificity for tumor antigens. In one embodiment, cytotoxic T cells are tested for their ability to kill target cells presenting tumor antigen peptide with MHC class I molecules. Target cells presenting tumor antigen peptide may be labeled and added to a suspension of T cells from a patient sample. The cytotoxicity may be measured by quantitating the release of label from lysed cells. Controls for spontaneous and total release may be included in the assay.

A cell presenting a peptide may be detected and its quantity determined by testing for its ability to induce a cellular response, e.g. to activate T cells, or measuring lysis of cells by CTLs having specificity for such cell.

The presence of said nucleic acid, said peptide, said antibody, said T cell and/or said cell which is to be detected and/or the quantity of which is to be determined and/or a quantity of said nucleic acid, said peptide, said antibody, said T cell and/or said cell which is increased compared to a reference level, e.g. compared to a patient without a tumor disease, may indicate the presence of or risk for (i.e. a potential for a development of) a tumor disease in said patient.

In one embodiment, the biological sample is from a tissue or organ wherein the cells when the tissue or organ is free of tumors do not substantially express a tumor antigen identified according to the invention and/or a tumor nucleic acid identified according to the invention. The indication of the presence of or risk for a tumor disease in a patient by the methods of the invention may indicate that the tumor disease is in said tissue or organ or that said tissue or organ is at risk for said tumor disease.

The methods of monitoring according to the invention preferably comprise a detection of and/or determination of the quantity of one or more of the parameters mentioned above in a first sample at a first point in time and in a further sample at a second point in time, wherein the regression, progression, course and/or onset of a tumor disease may be determined by comparing the two samples.

A quantity of said nucleic acid, said peptide, said antibody, said T cell and/or said cell which is decreased in a biological sample compared to a biological sample taken earlier from a patient may indicate a regression, a positive course, e.g. a successful treatment, or a reduced risk for an onset of a tumor disease in said patient.

In one embodiment, the biological sample is from a tissue or organ wherein the cells when the tissue or organ is free of tumors do not substantially express a tumor antigen identified according to the invention and/or a tumor nucleic acid identified according to the invention. In one embodiment, the tumor disease is in said tissue or organ.

A quantity of said nucleic acid, said peptide, said antibody, said T cell and/or said cell which is increased in a biological sample compared to a biological sample taken earlier from a patient may indicate a progression, a negative course, e.g. an unsuccessful treatment, recurrence or metastatic behaviour, an onset or a risk for an onset of a tumor disease in said patient.

In one embodiment, the biological sample is from a tissue or organ wherein the cells when the tissue or organ is free of tumors do not substantially express a tumor antigen identified according to the invention and/or a tumor nucleic acid identified according to the invention. In one embodiment, the tumor disease is in said tissue or organ.

In a particular aspect, the invention relates to a method for detection, i.e. determining the position or site, of a tumor disease, e.g. a particular tissue or organ. In one embodiment said method comprises administering an antibody which binds to a tumor antigen identified according to the present invention and which is coupled to a detectable label to a patient. The antibody may be a monoclonal antibody. In further embodiments, the antibody is a chimeric, human or humanized antibody, a fragment of an antibody or a synthetic antibody.

Labelling of a tissue or organ in said patient may indicate the presence of or risk for a tumor disease in said tissue or organ.

In one embodiment, the tissue or organ is a tissue or organ wherein the cells when the tissue or organ is free of tumors do not substantially express a tumor antigen identified according to the invention and/or a tumor nucleic acid identified according to the invention.

A positive diagnosis of a tumor disease as described above using the methods of the present invention may indicate a tumor disease which is amenable to the methods of treatment described herein.

A further object of this invention relates to diagnostic test kits useful in the methods for diagnosis, detection or monitoring of the invention. These kits in one embodiment comprise a ligand that specifically binds to a target molecule as defined above and, optionally, a detectable label, e.g. indicator enzymes, a radiolabels, fluorophores, or paramagnetic particles. In a particular embodiment, the ligand comprises nucleic acid primers or probes specific for target nucleic acids as described above, or an antibody or a derivative thereof, specific for a target peptide as described above. Kits may include informative pamphlets, for example, pamphlets informing one how to use reagents to practice a method disclosed herein.

In a further aspect, the invention relates to a peptide comprising the amino acid sequence of a tumor antigen peptide derived from of a tumor antigen identified according to the invention, or a derivative of said peptide. In one embodiment, said peptide comprises an amino acid sequence selected from the group consisting of SEQ ID NOs: 5 to 62 of the sequence listing, or a variant of said amino acid sequence.

In a further aspect, the invention relates to a recombinant nucleic acid molecule, in particular DNA or RNA molecule, which comprises a nucleic acid which codes for said peptide comprising the amino acid sequence of a tumor antigen peptide.

The invention also relates to host cells which comprise a recombinant nucleic acid molecule of the invention. Preferably, such host cells express the encoded peptide.

The host cell may be a recombinant cell and may secrete the encoded peptide, may express it on the surface and preferably may additionally express an WIC molecule which binds to said peptide or a procession product thereof. In one embodiment, the host cell expresses the WIC molecule endogenously. In a further embodiment, the host cell expresses the WIC molecule and/or the peptide or the procession product thereof in a recombinant manner. The host cell is preferably nonproliferative. In a preferred embodiment, the host cell is an antigen-presenting cell, in particular a dendritic cell, a monocyte or a macrophage.

In a further aspect, the invention relates to an agent which binds to a peptide comprising the amino acid sequence of a tumor antigen identified according to the invention or of a tumor antigen peptide derived from said tumor antigen, or a derivative of said peptide. In a preferred embodiment, the agent is a protein or peptide, in particular an antibody, a T cell receptor or an WIC molecule. In further embodiments, the antibody is a monoclonal, chimeric, human or humanized antibody, an antibody produced by combinatory techniques, a fragment of an antibody, or a synthetic antibody.

The invention furthermore relates to a conjugate between an agent of the invention which binds to a peptide comprising the amino acid sequence of a tumor antigen identified according to the invention or of a tumor antigen peptide derived from said tumor antigen, or a derivative of said peptide and a therapeutic effector moiety or a detectable label.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, 2$^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Some aspects of the present invention envision the immunotherapy of tumor diseases, in particular cancer diseases, in particular tumor or cancer diseases of the central nervous system such as glioma, in particular glioblastoma, utilizing the tumor nucleic acids and tumor antigens identified according to the invention by means of active or passive immunotherapeutic approaches which can be summarized as follows:

Immunotherapy

I. Active Immunotherapy ("Cancer Vaccines")
Immunisation with:
i) antigen or peptide (native or modified)
ii) nucleic acid encoding the antigen or peptide
iii) recombinant cells encoding the antigen or peptide
iv) recombinant viruses encoding the antigen or peptide
v) antigen presenting cells pulsed with antigen or peptide (native or modified) or transfected with nucleic acids encoding the antigen or peptide II. Passive Immunotherapy ("Adoptive Immunotherapy")
vi) Transfer of antibodies or T cell receptors that recognise antigen
vii) Transfer of cells sensitized in vitro to antigen (bulk or cloned populations)
viii) Transfer of effector cells (or stem cells) transduced with nucleic acids encoding T cell receptors that recognise antigen and preferably are responsive to tumor-specific class I MHC presented peptides In the past few years, much attention has been given to the role of CD8+ T cells in tumor immunity. Tumor-specific CD8+ CTLs have been shown to be capable of lysing tumor cells directly and eradicating tumor masses in vivo in animal models. However, CD4+ T cells are also thought to play a critical role and it may be that optimal cancer vaccines require the participation of both CD4+ and CD8+ T cells.

Immunisation with intact or substantially intact tumor antigen has the potential advantage of simultaneously immunising against both class I and class II epitopes but requires extensive and time-consuming efforts to purify large amounts of tumor antigen. The identification of MHC class I and class II peptides within a tumor antigen makes it possible to immunise with high levels of pure synthetic peptide. The peptide approach also has the advantage that one can choose between a MHC class I and a class II type response (or mixture) by choosing which epitopes to use. Immunisation with peptide also means that subdominant and/or cryptic epitopes can be chosen (as the need for antigen processing may be bypassed or reduced to a "trimming" role) in order to stimulate a different subset of T cells. Also the peptide may be modified (for example at their HLA class I or II anchor sites) to increase its immunogenicity.

The invention relates to tumor-specific class I MHC presented peptides and methods of using the same, as well as cytotoxic T lymphocytes (CTLs) responsive to tumor-specific class I MEW presented peptides and methods of using the same.

In one aspect, the invention provides anti-tumor vaccines capable of stimulating a cellular response against a tumor characterized by presentation of a tumor antigen identified according to the invention with class I MEW. The anti-tumor vaccines of the invention preferably comprise a tumor antigen peptide, or a tumor antigen peptide nucleic acid.

The invention also encompasses the use of nucleic acids encoding one or more of the tumor antigens identified according to the invention or one or more tumor antigen peptides derived therefrom. It is anticipated that the antigens or peptides so encoded are effective as therapeutic or prophylactic anti-tumor vaccines. For example, a particular contemplated application of these nucleic acids involves the induction of a cellular response such as a CTL response and/or a humoral immune response against such antigens.

Immunization with plasmid DNA can elicit antigen-specific immune responses consisting of CD8+ T cells, CD4+ T cells, and antibodies. DNA can be administered by the gene gun method of immunization. In gene gun immunization, plasmid DNA may be coated onto gold particles followed by delivery of the DNA-coated particles into the skin by a high-pressure, helium-driven gene gun.

Advances in molecular biology have made it possible to construct recombinant viruses that encode tumor antigens or tumor antigen peptides as described herein. Several recombinant viral vaccines have been used up to now.

Several viral vectors have shown promising results with regard to their potential to enhance immunotherapy of malignant diseases. Replication competent and replication incompetent viruses can be used, with the latter group being preferred. Herpes virus, adenovirus, vaccinia, reovirus, and New Castle Disease viruses are examples of preferred viruses useful according to the present invention.

Antigen presenting cells (APC) such as dendritic cells (DCs) can be loaded with either MHC class I-presented peptides or tumor lysate, or transduced with nucleic acid such as by transduction using adenovirus encoding a tumor antigen.

In a preferred embodiment, an anti-tumor vaccine of the invention comprises an APC loaded with tumor antigen peptide. In this respect, protocols may rely on in vitro culture/differentiation of DCs manipulated in such a way that they artificially present tumor antigen peptide. Production of genetically engineered DCs may involve introduction of nucleic acids encoding tumor antigens or tumor antigen peptides into DCs. Transfection of DCs with mRNA is a promising antigen-loading technique of stimulating strong antitumor immunity.

Dendritic cells (DCs) are leukocyte populations that present antigens captured in peripheral tissues to T cells via both MHC class II and I antigen presentation pathways. It is well known that DCs are potent inducers of immune responses and the activation of these cells is a critical step for the induction of antitumoral immunity. DC maturation is referred to as the status of DC activation at which such antigen-presenting DCs leads to T-cell priming, while its presentation by immature DCs results in tolerance. DC maturation is chiefly caused by biomolecules with microbial features detected by innate receptors (bacterial DNA, viral RNA, endotoxin, etc), pro-inflammatory cytokines (TNF, IL-1, IFNs), ligation of CD40 on the DC surface by CD40L, and substances released from cells undergoing stressful cell death. The DCs can be derived by culturing bone marrow cells in vitro with cytokines, such as granulocyte-macrophage colony-stimulating factor (GM-CSF) and tumor necrosis factor alpha.

Yet another embodiment of the invention comprises the preparation of antibodies, preferably monoclonal antibodies against a target antigen as defined above. Such monoclonal antibodies may be produced by conventional methods and include fragments or derivatives thereof, including, without limitation, human monoclonal antibodies, humanized monoclonal antibodies, chimeric monoclonal antibodies, single chain antibodies, e.g., scFv's and antigen-binding antibody fragments such as Fab and Fab' fragments. Methods for the preparation of monoclonal antibodies are known in the art. In general, the preparation of monoclonal antibodies comprises immunization of an appropriate host with the subject antigens, isolation of immune cells therefrom, use of such immune cells to isolate monoclonal antibodies and screening for monoclonal antibodies that specifically bind to either of such antigens. Antibody fragments may be prepared by known methods, e.g., enzymatic cleavage of monoclonal antibodies.

These monoclonal antibodies and fragments are useful for passive anti-tumor immunotherapy, or may be attached to therapeutic effector moieties, e.g., radiolabels, cytotoxins, therapeutic enzymes, agents that induce apoptosis, and the like in order to provide for targeted cytotoxicity, i.e., killing of tumor cells. In one embodiment of the present invention, such antibodies or fragments are administered in labeled or unlabeled form, alone or in conjunction with other therapeutics, e.g., chemotherapeutics such as cisplatin, methotrexate, adriamycin, and the like suitable for cancer therapy.

If used for passive anti-tumor immunotherapy, antibodies may or may not be attached to therapeutic effector moieties. Preferably the antibodies described herein mediate killing of cells by inducing complement dependent cytotoxicity (CDC) mediated lysis, antibody dependent cellular cytotoxicity (ADCC) mediated lysis, apoptosis, homotypic adhesion, and/or phagocytosis, preferably by inducing CDC mediated lysis and/or ADCC mediated lysis. The antibodies described herein preferably interact with components of the immune system, preferably through ADCC or CDC. However, antibodies of the invention may also exert an effect simply by binding to tumor antigens on the cell surface, thus, e.g. blocking proliferation of the cells.

ADCC describes the cell-killing ability of effector cells as described herein, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that also leads to antigen presentation and the induction of tumor-directed T-cell responses. Preferably, in vivo induction of ADCC will lead to tumor-directed T-cell responses and host-derived antibody responses.

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell and may lead to apoptosis.

Passive immunotherapy with immune cells (optionally genetically modified) capable of recognizing tumor antigens is effective in mediating the regression of cancer in selected patients. These techniques may be based on ex-vivo reactivation and expansion of cloned or polyclonal cultures of tumor reactive T cells. After culture, T cells may be reinfused into the patient along with IL-2. In vitro techniques have been developed in which human lymphocytes are sensitized in vitro to tumor antigen peptides presented on antigen presenting cells. By repetitive in vitro stimulation cells can be derived with a great capacity to recognize human tumor antigens. The adoptive transfer of these cells may be more effective in mediating tumor regression in vivo than are conventionally grown cells.

In one embodiment, autologous cytotoxic lymphocytes or tumor infiltrating lymphocytes may be obtained from a patient with cancer. The lymphocytes may be grown in culture and tumor antigen-responsive CTLs expanded by culturing in the presence of tumor antigen peptide presented with WIC class I, alone or in combination with at least one immunomodulatory agent, preferably additionally with cytokines. The tumor antigen-responsive CTLs are then infused back into the patient in an amount effective to reduce or eliminate the tumors in the patient.

Patients could be pre-stimulated with an anti-tumor peptide vaccine prior lymphocyte harvest if the existing response was inadequate. It is expected that the adoptively transferred CTLs would survive best with IL-2 infusion at low to intermediate doses.

By "tumor antigen-responsive CTL" is meant a CD8+ T cell that is responsive to a tumor antigen peptide derived from said tumor antigen, which is presented with class I WIC, e.g. on the surface of tumor cells.

According to the invention, CTL responsiveness may include sustained calcium flux, cell division, production of cytokines such as IFN-gamma and TNF-alpha, upregulation of activation markers such as CD44 and CD69, and specific cytolytic killing of tumor antigen expressing target cells. CTL responsiveness may also be determined using an artificial reporter that accurately indicates CTL responsiveness.

By "tumor antigen peptide" or "tumor antigen peptide derived from a tumor antigen" is meant an oligopeptide or polypeptide comprising an amino acid sequence substantially corresponding to the amino acid sequence of a fragment or peptide of a tumor antigen identified according to the present invention. Preferably, a tumor antigen peptide is capable of stimulating a cellular response against a tumor characterized by presentation of a tumor antigen identified herein with class I WIC and preferably a tumor antigen-responsive CTL and/or of eliciting antibodies that specifically bind to a tumor antigen identified according to the present invention when used itself or attached to an immunogenic carrier. A tumor antigen peptide according to the invention preferably is a peptide comprising a sequence substantially corresponding to the sequence of a fragment of the amino acid sequence according to SEQ ID NO: 3 or 4 of the sequence listing or is a derivative of said peptide. In one embodiment, said peptide comprises an amino acid sequence selected from the group consisting of SEQ ID NOs: 5 to 62 of the sequence listing, or a variant of said amino acid sequence. A tumor antigen peptide may be of any length.

If a tumor antigen peptide is to be presented directly, i.e. without processing, in particular without cleavage, it has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably the sequence of a tumor antigen peptide which is to be presented directly is derived from the amino acid sequence of a tumor antigen identified according to the invention, i.e. its sequence substantially corresponds and is preferably completely identical to a fragment of a tumor antigen identified according to the invention. If a tumor antigen peptide is to be presented following processing, in particular following cleavage, the peptide produced by processing has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably the sequence of the peptide which is to be presented following processing is derived from the amino acid sequence of a tumor antigen identified according to the invention, i.e. its sequence substantially corresponds and is preferably completely identical to a fragment of a tumor antigen identified according to the invention. Thus, a tumor antigen peptide according to the invention in one embodiment comprises a sequence of 7-20 amino acids in length, more preferably 7-12 amino acids in length, more preferably 8-11 amino acids in length, in particular 9 or 10 amino acids in length which substantially corresponds and is preferably completely identical to a fragment of a tumor antigen identified according to the invention and following processing of the tumor antigen peptide makes up the presented peptide. However, the tumor antigen peptide may also comprise a sequence which substantially corresponds and preferably is completely identical to a fragment of a tumor antigen identified according to the invention which is even longer than the above stated sequence. In one embodiment, a tumor antigen peptide may comprise the entire sequence of a tumor antigen identified according to the invention.

Preferably, a tumor antigen peptide may be presented, directly or following processing, with class I MHC molecules, and when so presented is capable of stimulating a tumor antigen-responsive CTL. Peptides having amino acid sequences substantially corresponding to a sequence of a peptide which is presented by the class I MHC may differ at one or more residues that are not essential for TCR recognition of the peptide as presented by the class I MHC, or for peptide binding to MHC. Such substantially corresponding peptides are also capable of stimulating a tumor antigen-responsive CTL. Peptides having amino acid sequences differing from a presented peptide at residues that do not affect TCR recognition but improve the stability of binding to MHC may improve the immunogenicity of the tumor antigen peptide, and may be referred to herein as "optimized peptides". Using existing knowledge about which of these residues may be more likely to affect binding either to the MHC or to the TCR, a rational approach to the design of substantially corresponding peptides may be employed. Resulting peptides that are functional are contemplated as tumor antigen peptides.

According to the invention, the term "immunoreactive cell" means a cell which can mature into an immune cell (such as B cell, T helper cell, or CTL (cytolytic T cell)) with suitable stimulation. Immunoreactive cells comprise CD34$^+$ hematopoietic stem cells, immature and mature T cells and immature and mature B cells. If production of cytolytic or T helper cells recognizing a tumor antigen is desired, the immunoreactive cell is contacted with a cell presenting a tumor antigen or tumor antigen peptide derived from the tumor antigen (e.g. a cell expressing a tumor antigen) under conditions which favor production, differentiation and/or selection of cytolytic T cells and of T helper cells. The differentiation of T cell precursors into a cytolytic T cell, when exposed to an antigen, is similar to clonal selection of the immune system.

The terms "T cell" and "T lymphocyte" are used interchangeably herein and include T helper cells (CD4+ T cells) and cytotoxic T cells (CTLs, CD8+ T cells) which comprise cytolytic T cells.

By "cell characterized by presentation of a tumor antigen with class I MHC" or "cell presenting a tumor antigen with class I MHC" or similar expressions is meant a cell such as a tumor cell or an antigen presenting cell presenting the tumor antigen it expresses or a fragment derived from said tumor antigen, e.g. by processing of the tumor antigen, in the context of MHC Class I molecules. Similarly, the term "tumor characterized by presentation of a tumor antigen with class I MHC" denotes a tumor comprising cells characterized by presentation of a tumor antigen with class I MHC.

By "fragment of a tumor antigen identified according to the invention which is presented" or similar expressions is meant that the fragment can be presented by MHC class I or class II, preferably MHC class I, e.g. when added directly to antigen presenting cells. In one embodiment, the fragment is a fragment which is naturally presented by cells expressing a tumor antigen identified according to the invention, e.g. tumor cells.

By "cell that recognizes a tumor antigen or a tumor antigen peptide derived from said tumor antigen" or "immunoreactive cell that recognizes a tumor antigen or a tumor antigen peptide derived from said tumor antigen" or similar expressions is meant a cell that is able to recognize said tumor antigen or a tumor antigen peptide derived from said tumor antigen with some degree of specificity, in particular if presented in the context of MHC molecules such as on the surface of antigen presenting cells or tumor cells. Preferably, said recognition enables the cell that recognizes a tumor antigen or a tumor antigen peptide derived from said tumor antigen to be responsive. If the cell is a helper T cell (CD4+ T cell) bearing receptors that recognize a tumor antigen or a tumor antigen peptide derived from said tumor antigen in the context of MHC class II molecules such responsiveness may involve the release of cytokines and/or the activation of CD8+ lymphocytes (CTLs) and/or B cells. If the cell is a CTL such responsiveness may involve the elimination of cells presented in the context of MHC class I molecules, i.e. cells characterized by presentation of a tumor antigen with class I MHC, for example via apoptosis or perforin-mediated cell lysis. Such CTL that recognizes a tumor antigen or a tumor antigen peptide derived from said tumor antigen and are responsive are also termed "tumor antigen-responsive CTL" herein. If the cell is a B cell such immune such responsiveness may involve the release of immunoglobulins.

By "T cell receptor that recognizes a tumor antigen or a tumor antigen peptide derived from said tumor antigen" is meant a T cell receptor that is able to recognize said tumor antigen or a tumor antigen peptide derived from said tumor antigen with some degree of specificity, in particular if presented in the context of MHC molecules. Preferably, said recognition enables the cell carrying the T cell receptor that recognizes a tumor antigen or a tumor antigen peptide derived from said tumor antigen to be responsive as outlined above.

A "cellular response against a tumor antigen" is meant to include a cellular response directed to cells characterized by presentation of a tumor antigen with class I or class II MHC. The cellular response relates to cells called T cells or T lymphocytes which act as either 'helpers' or 'killers'. The helper T cells (also termed CD4+ T cells) play a central role by regulating the immune response and the killer cells (also termed cytotoxic T cells, cytolytic T cells, CD8+ T cells or CTLs) kill tumor cells, preventing the production of more tumor cells. Although both arms of the immune response are thought to be necessary, the CTL response may be more important for controlling cancer.

Some therapeutic methods are based on a reaction of the immune system of a patient, which results in a lysis of diseased cells such as cancer cells which present a tumor antigen with class I MHC. In this connection, for example autologous cytotoxic T lymphocytes specific for a complex of a tumor antigen peptide and an MHC molecule may be administered to a patient having a tumor disease. The production of such cytotoxic T lymphocytes in vitro is known. An example of a method of differentiating T cells can be found in WO-A-9633265. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

In another method of selecting cytotoxic T lymphocytes, fluorogenic tetramers of MHC class I molecule/peptide complexes are used for obtaining specific clones of cytotoxic T lymphocytes (Altman et al., *Science* 274:94-96, 1996; Dunbar et al., *Curr. Biol.* 8:413-416, 1998).

Furthermore, cells presenting the desired complex (e.g. dendritic cells) may be combined with cytotoxic T lymphocytes of healthy individuals or another species (e.g. mouse) which may result in propagation of specific cytotoxic T lymphocytes with high affinity. The high affinity T cell receptor of these propagated specific T lymphocytes may be cloned and optionally humanized to a different extent, and the T cell receptors thus obtained then transduced via gene transfer, for example using retroviral vectors, into T cells of patients. Adoptive transfer may then be carried out using these genetically altered T lymphocytes (Stanislawski et al., Nat Immunol. 2:962-70, 2001; Kessels et al., Nat Immunol. 2:957-61, 2001).

Cytotoxic T lymphocytes may also be generated in vivo in a manner known per se. One method uses nonproliferative cells expressing an MHC class I/peptide complex. The cells used here will be those which usually express the complex, such as irradiated tumor cells or cells transfected with one or both genes necessary for presentation of the complex (i.e. the antigenic peptide and the presenting MHC molecule). Another preferred form is the introduction of the tumor antigen in the form of recombinant RNA which may be introduced into cells by liposomal transfer or by electroporation, for example. The resulting cells present the complex of interest and are recognized by autologous cytotoxic T lymphocytes which then propagate.

A similar effect can be achieved by combining a tumor antigen or a tumor antigen peptide with an adjuvant in order to make incorporation into antigen-presenting cells in vivo possible. The tumor antigen or tumor antigen peptide may be represented as protein, as DNA (e.g. within a vector) or as RNA. The tumor antigen may be processed to produce a peptide partner for the MHC molecule, while a fragment thereof may be presented without the need for further processing. The latter is the case in particular, if these can bind to MHC molecules. Preference is given to administration forms in which the complete antigen is processed in vivo by a dendritic cell, since this may also produce T helper cell responses which are needed for an effective immune response (Ossendorp et al., *Immunol Lett.* 74:75-9, 2000; Ossendorp et al., *J. Exp. Med.* 187:693-702, 1998). In general, it is possible to administer an effective amount of the tumor antigen to a patient by intradermal injection, for example. However, injection may also be carried out intranodally into a lymph node (Maloy et al., *Proc Natl Acad Sci USA* 98:3299-303, 2001).

According to the invention, a "reference" such as a reference sample or reference organism may be used to correlate and compare the results obtained in the methods of the invention from a test sample or test organism, i.e. a patient. Typically the reference organism is a healthy organism, in particular an organism which does not suffer from a tumor disease.

A "reference value" or "reference level" can be determined from a reference empirically by measuring a sufficiently large number of references. Preferably the reference value is determined by measuring at least 2, preferably at least 3, preferably at least 5, preferably at least 8, preferably at least 12, preferably at least 20, preferably at least 30, preferably at least 50, or preferably at least 100 references.

According to the invention, the term "binding" preferably relates to a specific binding. "Specific binding" means that an agent such as an antibody binds stronger to a target such as an epitope for which it is specific compared to the binding to another target. An agent binds stronger to a first target compared to a second target if it binds to the first target with a dissociation constant ($K_D$) which is lower than the dissociation constant for the second target. Preferably the dissociation constant ($K_D$) for the target to which the agent binds specifically is more than $10^2$-fold, $10^3$-fold, $10^4$-fold, $10^5$-fold, $10^6$-fold, $10^7$-fold, $10^8$-fold, $10^9$-fold, or $10^{10}$-fold lower than the dissociation constant ($K_D$) for the target to which the agent does not bind specifically.

The term "COL20A1" relates to a collagen gene, preferably a human collagen gene. Preferably, the term "COL20A1" relates to a nucleic acid comprising, preferably consisting of the nucleic acid sequence of SEQ ID NO: 1 or 2 of the sequence listing or a variant of said nucleic acid sequence and to a protein encoded by this nucleic acid, preferably to a protein comprising, preferably consisting of the amino acid sequence of SEQ ID NO: 3 or 4 of the sequence listing or a variant of said amino acid sequence.

According to the invention a tumor nucleic acid or a tumor antigen is associated with a cell or tumor if said tumor nucleic acid or tumor antigen is spatially linked to said cell or tumor, in particular if said tumor nucleic acid or tumor antigen is present in said cell or tumor. Said tumor nucleic acid or tumor antigen may be expressed by said cell or tumor. Said cells may be a tumor cell or a cell being associated with tumor cells such as a stroma cell.

According to the invention, a nucleic acid is preferably deoxyribonucleic acid (DNA) or ribonucleic acid (RNA). Nucleic acids comprise according to the invention genomic DNA, cDNA, mRNA, recombinantly produced and chemically synthesized molecules. According to the invention, a nucleic acid may be present as a single-stranded or double-stranded and linear or covalently circularly closed molecule.

The terms "tumor nucleic acid identified according to the invention" and "nucleic acid encoding a tumor antigen identified according to the invention" have similar meanings.

As used herein, the term "RNA" means a molecule comprising ribonucleotide residues. By "ribonucleotide" is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

If reference is made herein to the detection of or the determination of the quantity of a nucleic acid, the nucleic acid which is actually to be detected or the quantity of which is actually to be determined is preferably mRNA. However, it should be understood that this may also include embodiments wherein mRNA is detected or the quantity of mRNA is determined indirectly. For example, mRNA may be transformed into cDNA and the cDNA detected or its quantity determined. mRNA is given herein as the cDNA equivalent. One skilled in the art would understand that the cDNA sequence is equivalent to the mRNA sequence, and can be used for the same purpose herein, e.g., the generation of probes hybridizing to the nucleic acid to be detected. Thus, if reference is made herein to the sequences shown in the sequence listing this is also to include the RNA equivalents of said sequences.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

The term "variant" with respect to, for example, nucleic acid and amino acid sequences, according to the invention includes any variants, in particular mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence.

With respect to nucleic acid molecules, the term "variant" includes degenerate nucleic acid sequences, wherein a degenerate nucleic acid according to the invention is a nucleic acid that differs from a reference nucleic acid in codon sequence due to the degeneracy of the genetic code.

Furthermore, a "variant" of a specific nucleic acid sequence according to the invention includes nucleic acid sequences comprising single or multiple such as at least 2, at least 4, or at least 6 and preferably up to 3, up to 4, up to 5, up to 6, up to 10, up to 15, or up to 20 nucleotide substitutions, deletions and/or additions.

Preferably the degree of identity between a given nucleic acid sequence and a nucleic acid sequence which is a variant of said given nucleic acid sequence will be at least 70%, preferably at least 75%, preferably at least 80%, more preferably at least 85%, even more preferably at least 90% or most preferably at least 95%, 96%, 97%, 98% or 99%. The degree of identity is preferably given for a region of at least about 30, at least about 50, at least about 70, at least about 90, at least about 100, at least about 150, at least about 200, at least about 250, at least about 300, or at least about 400 nucleotides. In preferred embodiments, the degree of identity is given for the entire length of the reference nucleic acid sequence.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The term "percentage identity" is intended to denote a percentage of nucleotides or of amino acid residues which are identical between the two sequences to be compared, obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

A nucleic acid is "capable of hybridizing" or "hybridizes" to another nucleic acid if the two sequences are complementary with one another. A nucleic acid is "complementary" to another nucleic acid if the two sequences are capable of forming a stable duplex with one another. According to the invention, hybridization is preferably carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or "fully complementary" means that all the contiguous residues of a nucleic acid sequence will hydrogen bond with the same number of contiguous residues in a second nucleic acid sequence. Preferably, the degree of complementarity according to the invention is at least 70%, preferably at least 75%, preferably at least 80%, more preferably at least 85%, even more preferably at least 90% or most preferably at least 95%, 96%, 97%, 98% or 99%. Most preferably, the degree of complementarity according to the invention is 100%.

The term "derivative" comprises any chemical derivatization of a nucleic acid on a nucleotide base, on the sugar or on the phosphate. The term "derivative" also comprises nucleic acids which contain nucleotides and nucleotide analogs not occurring naturally. Preferably, a derivatization of a nucleic acid increases its stability.

Nucleic acids coding for tumor antigens or tumor antigen peptides may, according to the invention, be present alone or in combination with other nucleic acids, in particular heterologous nucleic acids. Preferably, a nucleic acid coding for a tumor antigen or tumor antigen peptide expresses said tumor antigen or tumor antigen peptide. In preferred embodiments, a nucleic acid is functionally linked to expression control sequences or regulatory sequences which may be homologous or heterologous with respect to said nucleic acid. A coding sequence and a regulatory sequence are "functionally" linked to one another, if they are covalently linked to one another in such a way that expression or transcription of said coding sequence is under the control or under the influence of said regulatory sequence. If the coding sequence is to be translated into a functional protein, then, with a regulatory sequence functionally linked to said coding sequence, induction of said regulatory sequence results in transcription of said coding sequence, without causing a frame shift in the coding sequence or said coding sequence not being capable of being translated into the desired protein or peptide.

The term "expression control sequence" or "regulatory sequence" comprises according to the invention promoters, enhancers and other control elements which regulate expression of a gene. In particular embodiments of the invention, the expression control sequences can be regulated. The exact structure of regulatory sequences may vary as a function of the species or cell type, but generally comprises 5'untranscribed and 5'untranslated sequences which are involved in initiation of transcription and translation, respectively, such as TATA box, capping sequence, CAAT sequence, and the like. More specifically, 5'untranscribed regulatory sequences comprise a promoter region which includes a promoter sequence for transcriptional control of the functionally linked gene. Regulatory sequences may also comprise enhancer sequences or upstream activator sequences.

According to the invention, a nucleic acid may furthermore be present in combination with another nucleic acid which codes for a peptide controlling secretion of the protein or peptide encoded by said nucleic acid from a host cell. According to the invention, a nucleic acid may also be present in combination with another nucleic acid which codes for a peptide causing the encoded protein or peptide to be anchored on the cell membrane of the host cell or compartmentalized into particular organelles of said cell. Similarly, a combination with a nucleic acid is possible which represents a reporter gene or any "tag".

In a preferred embodiment, a recombinant nucleic acid molecule is according to the invention a vector, where appropriate with a promoter, which controls expression of a nucleic acid, for example a nucleic acid coding for a tumor antigen identified according to the invention. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. An intermediary vehicle may be adapted, for example, to the use in electroporation, in bombardment with microprojectiles, in liposomal administration, in the transfer with the aid of agrobacteria or in insertion via DNA or RNA viruses. Vectors comprise plasmids, phagemids, bacteriophages or viral genomes.

The nucleic acids coding for a tumor antigen identified according to the invention may be used for transfection of host cells. Nucleic acids here mean both recombinant DNA and RNA. Recombinant RNA may be prepared by in-vitro transcription of a DNA template. Furthermore, it may be modified by stabilizing sequences, capping and polyadenylation prior to application.

According to the invention, the term "host cell" relates to any cell which can be transformed or transfected with an exogenous nucleic acid. The term "host cells" comprises according to the invention prokaryotic (e.g. *E. coli*) or eukaryotic cells (e.g. dendritic cells, B cells, CHO cells, COS cells, K562 cells, yeast cells and insect cells). Particular preference is given to mammalian cells such as cells from humans, mice, hamsters, pigs, goats, primates. The cells may be derived from a multiplicity of tissue types and comprise primary cells and cell lines. Specific examples comprise keratinocytes, peripheral blood leukocytes, stem cells of the bone marrow and embryonic stem cells. In further embodiments, the host cell is an antigen-presenting cell, in particular a dendritic cell, monocyte or a macrophage. A nucleic acid may be present in the host cell in the form of a single copy or of two or more copies and, in one embodiment, is expressed in the host cell.

According to the invention, the term "expression" is used in its most general meaning and comprises the production of RNA or of RNA and protein. It also comprises partial expression of nucleic acids. Furthermore, expression may be carried out transiently or stably. Preferred expression systems in mammalian cells comprise pcDNA3.1, pcDNA3.3 and pRc/CMV (Invitrogen, Carlsbad, Calif.), which contain a selectable marker such as a gene imparting resistance to G418 (and thus enabling stably transfected cell lines to be selected) and the enhancer-promoter sequences of cytomegalovirus (CMV).

In those cases of the invention in which an MHC molecule presents a tumor antigen or a tumor antigen peptide, an expression vector may also comprise a nucleic acid sequence coding for said MHC molecule. The nucleic acid sequence coding for the MHC molecule may be present on the same expression vector as the nucleic acid coding for the tumor antigen or the tumor antigen peptide, or both nucleic acids may be present on different expression vectors. In the latter case, the two expression vectors may be cotransfected into a cell. If a host cell expresses neither the tumor antigen or the tumor antigen peptide nor the MHC molecule, both nucleic acids coding therefor may be transfected into the cell either on the same expression vector or on different expression vectors. If the cell already expresses the MHC molecule, only the nucleic acid sequence coding for the tumor antigen or the tumor antigen peptide can be transfected into the cell.

"Antisense molecules" or "antisense nucleic acids" may be used for regulating, in particular reducing, expression of a nucleic acid. The term "antisense molecule" or "antisense nucleic acid" refers according to the invention to an oligonucleotide which is an oligoribonucleotide, oligodeoxyribonucleotide, modified oligoribonucleotide or modified oligodeoxyribonucleotide and which hybridizes under physiological conditions to DNA comprising a particular gene or to mRNA of said gene, thereby inhibiting transcription of said gene and/or translation of said mRNA. According to the invention, an "antisense molecule" also comprises a construct which contains a nucleic acid or a part thereof in reverse orientation with respect to its natural promoter. An antisense transcript of a nucleic acid or of a part thereof may form a duplex with naturally occurring mRNA and thus prevent accumulation of or translation of the mRNA. Another possibility is the use of ribozymes for inactivating a nucleic acid.

In preferred embodiments, the antisense oligonucleotide hybridizes with an N-terminal or 5' upstream site such as a translation initiation site, transcription initiation site or promoter site. In further embodiments, the antisense oligonucleotide hybridizes with a 3'untranslated region or mRNA splicing site.

In one embodiment, an oligonucleotide of the invention consists of ribonucleotides, deoxyribonucleotides or a combination thereof, with the 5' end of one nucleotide and the 3' end of another nucleotide being linked to one another by a phosphodiester bond. These oligonucleotides may be synthesized in the conventional manner or produced recombinantly.

In preferred embodiments, an oligonucleotide of the invention is a "modified" oligonucleotide. Here, the oligonucleotide may be modified in very different ways, without impairing its ability to bind its target, in order to increase, for example, its stability or therapeutic efficacy. According to the invention, the term "modified oligonucleotide" means an oligonucleotide in which (i) at least two of its nucleotides are linked to one another by a synthetic internucleoside bond (i.e. an internucleoside bond which is not a phosphodiester bond) and/or (ii) a chemical group which is usually not found in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term "modified oligonucleotide" also comprises oligonucleotides having a covalently modified base and/or sugar. "Modified oligonucleotides" comprise, for example, oligonucleotides with sugar residues which are covalently bound to low molecular weight organic groups other than a hydroxyl group at the 3' position and a phosphate group at the 5' position. Modified oligonucleotides may comprise, for example, a 2'-O-alkylated ribose residue or another sugar instead of ribose, such as arabinose.

It is to be understood that all embodiments described above with respect to oligonucleotides may also apply to polynucleotides.

By "small interfering RNA" or "siRNA" as used herein is meant an isolated RNA molecule, preferably greater than 10 nucleotides in length, more preferably greater than 15 nucleotides in length, and most preferably 18, 19, 20, 21, 22, 23, 24, 25, 26, 27, 28, 29, or 30 nucleotides in length that is used to identify a target gene or mRNA to be degraded. A range of 19-25 nucleotides is the most preferred size for siRNAs.

siRNA according to the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA; modifications that make the siRNA resistant to nuclease digestion (e. g., the use of 2'-substituted ribonucleotides or modifications to the sugar-phosphate backbone); or the substitution of one or more nucleotides in the siRNA with deoxyribonucleotides. Furthermore, siRNA may be modified to increase the stability thereof as described above for modified oligonucleotides, in particular by introducing one or more phosphorothioate linkages.

One or both strands of the siRNA can also comprise a 3'-overhang. As used herein, a "3'-overhang" refers to at least one unpaired nucleotide extending from the 3'-end of an RNA strand. Thus in one embodiment, the siRNA comprises at least one 3'-overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length. In the embodiment in which both strands of the siRNA molecule comprise a 3'-overhang, the length of the overhangs can be the same or different for each strand. In a most preferred embodiment, the 3'-overhang is present on both strands of the siRNA, and is 2 nucleotides in length. For example, each strand of the siRNA of the invention can comprise 3'-overhangs of dideoxythymidylic acid ("TT") or diuridylic acid ("uu").

In order to enhance the stability of the siRNA, the 3'-overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3'-overhangs with 2'-deoxythymidine, is tolerated and does not affect the efficiency of RNAi degradation. In particular, the absence of a 2'-hydroxyl in the 2'-deoxythymidine significantly enhances the nuclease resistance of the 3'-overhang in tissue culture medium.

The sense and antisense strands of the siRNA can comprise two complementary, single-stranded RNA molecules or can comprise a single molecule in which two complementary portions are base-paired and are covalently linked by a single-stranded "hairpin" area. That is, the sense region and antisense region can be covalently connected via a linker molecule. The linker molecule can be a polynucleotide or non-nucleotide linker. Without wishing to be bound by any theory, it is believed that the hairpin area of the latter type of siRNA molecule is cleaved intracellularly by the "Dicer" protein (or its equivalent) to form a siRNA of two individual base-paired RNA molecules.

As used herein, "target mRNA" refers to an RNA molecule that is a target for downregulation.

siRNA can be expressed from pol III expression vectors without a change in targeting site, as expression of RNAs from pol III promoters is only believed to be efficient when the first transcribed nucleotide is a purine.

siRNA according to the invention can be targeted to any stretch of approximately 19-25 contiguous nucleotides in any of the target mRNA sequences (the "target sequence"). Techniques for selecting target sequences for siRNA are given, for example, in Tuschl T. et al., "The siRNA User Guide", revised Oct. 11, 2002, the entire disclosure of which is herein incorporated by reference. "The siRNA User Guide" is available on the world wide web at a website maintained by Dr. Thomas Tuschl, Laboratory of RNA Molecular Biology, Rockefeller University, New York, USA, and can be found by accessing the website of the Rockefeller University and searching with the keyword "siRNA". Thus, the sense strand of the present siRNA comprises a nucleotide sequence substantially identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3'-direction) from the start codon. The target sequence can, however, be located in the 5'- or 3'-untranslated regions, or in the region nearby the start codon.

siRNA can be obtained using a number of techniques known to those of skill in the art. For example, siRNA can be chemically synthesized or recombinantly produced using methods known in the art, such as the *Drosophila* in vitro system described in U.S. published application 2002/0086356 of Tuschl et al., the entire disclosure of which is herein incorporated by reference.

Preferably, siRNA is chemically synthesized using appropriately protected ribonucleoside phosphoramidites and a conventional DNA/RNA synthesizer. siRNA can be synthesized as two separate, complementary RNA molecules, or as a single RNA molecule with two complementary regions.

Alternatively, siRNA can also be expressed from recombinant circular or linear DNA plasmids using any suitable promoter. Such embodiments are included according to the present invention when reference is made herein to the administration of siRNA or the incorporation of siRNA into pharmaceutical compositions. Suitable promoters for expressing siRNA of the invention from a plasmid include, for example, the U6 or H1 RNA pol III promoter sequences and the cytomegalovirus promoter.

Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly. The use of recombinant plasmids to deliver siRNA to cells in vivo is discussed in more detail below. siRNA can be expressed from a recombinant plasmid either as two separate, complementary RNA molecules, or as a single RNA molecule with two complementary regions.

Selection of plasmids suitable for expressing siRNA, methods for inserting nucleic acid sequences for expressing the siRNA into the plasmid, and methods of delivering the recombinant plasmid to the cells of interest are within the skill in the art.

siRNA can also be expressed from recombinant viral vectors intracellularly in vivo. The recombinant viral vectors comprise sequences encoding the siRNA and any suitable promoter for expressing the siRNA sequences. The recombinant viral vectors can also comprise inducible or regulatable promoters for expression of the siRNA in a particular tissue or in a particular intracellular environment. siRNA can be expressed from a recombinant viral vector either as two separate, complementary RNA molecules, or as a single RNA molecule with two complementary regions.

The term "peptide" comprises oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

Preferably, the proteins and peptides described according to the invention have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo.

Such proteins and peptides may be used, for example, in producing antibodies and in an immunological or diagnostic assay or as therapeutics. Proteins and peptides described according to the invention may be isolated from biological samples such as tissue or cell homogenates and may also be expressed recombinantly in a multiplicity of pro- or eukaryotic expression systems.

For the purposes of the present invention, "variants" of a protein or peptide or of an amino acid sequence comprise amino acid insertion variants, amino acid deletion variants and/or amino acid substitution variants.

Amino acid insertion variants comprise amino- and/or carboxy-terminal fusions and also insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid deletion variants are characterized by the removal of one or more amino acids from the sequence.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties.

Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least 70%, preferably at least 80%, preferably at least 85%, even more preferably at least 90% or most preferably at least 95%, 96%, 97%, 98% or 99%. The degree of similarity or identity is given preferably for a region of at least about 20, at least about 40, at least about 60, at least about 80, at least about 100, at least about 120, at least about 140, at least about 160, at least about 200 or 250 amino acids. In preferred embodiments, the degree of similarity or identity is given for the entire length of the reference amino acid sequence.

The peptides and amino acid variants described herein may be readily prepared with the aid of known peptide synthesis techniques such as, for example, by solid phase synthesis (Merrifield, 1964) and similar methods or by recombinant DNA manipulation. The manipulation of DNA sequences for preparing proteins and peptides having substitutions, insertions or deletions, is described in detail in Sambrook et al. (1989), for example.

According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. The term "derivative" also extends to all functional chemical equivalents of said proteins and peptides. Preferably, a modified peptide has increased stability and/or increased immunogenicity.

According to the invention, a variant of a nucleic acid or amino acid sequence, a substantially corresponding amino acid sequence or a fragment or derivative of a peptide preferably has a functional property of the nucleic acid or amino acid sequence, the amino acid sequence or the peptide, respectively, from which it has been derived. Such functional properties comprise the interaction with antibodies, the interaction with other peptides or proteins, the selective binding of nucleic acids and an enzymatic activity. In one embodiment, a variant of a nucleic acid or amino acid sequence, a substantially corresponding amino acid sequence or a fragment or derivative of a peptide is immunologically equivalent to the nucleic acid or amino acid sequence, the amino acid sequence or the peptide, respectively, from which it has been derived. In one embodiment, the functional property is an immunological property. A particular property is the ability to form a complex with MHC molecules and, where appropriate, generate an immune response, preferably by stimulating cytotoxic or T helper cells. A fragment of a tumor antigen preferably comprises a sequence of at least 6, in particular at least 8, at least 10, at least 12, at least 15, at least 20, at least 30 or at least 50, consecutive amino acids of the tumor antigen. A fragment of a tumor antigen preferably comprises a sequence of up to 8, in particular up to 10, up to 12, up to 15, up to 20, up to 30 or up to 55, consecutive amino acids of the tumor antigen. A fragment of a tumor antigen is preferably a part of the tumor antigen which may be presented with MHC molecules and when so presented is capable of stimulating a cellular response.

Preferred fragments of a tumor antigen are suitable for the stimulation of cytotoxic T-lymphocytes in vivo but also for the production of expanded and stimulated T-lymphocytes for the therapeutic adoptive transfer ex vivo.

Antisera which contain specific antibodies specifically binding to the target protein can be prepared by various standard processes; see, for example, "Monoclonal Antibodies: A Practical Approach" by Philip Shepherd, Christopher Dean ISBN 0-19-963722-9; "Antibodies: A Laboratory Manual" by Ed Harlow, David Lane, ISBN: 0879693142 and "Using Antibodies: A Laboratory Manual: Portable Protocol NO" by Edward Harlow, David Lane, Ed Harlow ISBN 0879695447. Thereby it is also possible to generate affine and specific antibodies which recognize complex membrane proteins in their native form (Azorsa et al., J. Immunol. Methods 229: 35-48, 1999; Anderson et al., J. Immunol. 143: 1899-1904, 1989; Gardsvoll, J. Immunol.

Methods 234: 107-116, 2000). This is in particular relevant for the preparation of antibodies which are to be used therapeutically, but also for many diagnostic applications. In this respect, it is possible to immunize with the whole protein, with extracellular partial sequences as well as with cells which express the target molecule in physiologically folded form.

Monoclonal antibodies are traditionally prepared using the hybridoma technology. (for technical details see: "Monoclonal Antibodies: A Practical Approach" by Philip Shepherd, Christopher Dean ISBN 0-19-963722-9; "Antibodies: A Laboratory Manual" by Ed Harlow, David Lane ISBN: 0879693142; "Using Antibodies: A Laboratory Manual: Portable Protocol NO" by Edward Harlow, David Lane, Ed Harlow ISBN: 0879695447).

It is known that only a small part of an antibody molecule, the paratope, is involved in binding of the antibody to its epitope (cf. Clark, W. R. (1986), *The Experimental Foundations of Modern Immunology*, Wiley & Sons, Inc., New York; Roitt, I. (1991), *Essential Immunology*, 7th Edition, Blackwell Scientific Publications, Oxford). The pFc' and Fc regions are, for example, effectors of the complement cascade but are not involved in antigen binding. An antibody from which the pFc' region has been enzymatically removed or which has been produced without the pFc' region, referred to as F(ab')$_2$ fragment, carries both antigen binding sites of a complete antibody. Similarly, an antibody from which the Fc region has been enzymatically removed or which has been produced without said Fc region, referred to as Fab fragment, carries one antigen binding site of an intact antibody molecule. Furthermore, Fab fragments consist of a covalently bound light chain of an antibody and part of the heavy chain of said antibody, referred to as Fd. The Fd fragments are the main determinants of antibody specificity (a single Fd fragment can be associated with up to ten different light chains, without altering the specificity of the antibody) and Fd fragments, when isolated, retain the ability to bind to an epitope.

Located within the antigen-binding part of an antibody are complementary-determining regions (CDRs) which interact directly with the antigen epitope and framework regions (FRs) which maintain the tertiary structure of the paratope. Both the Fd fragment of the heavy chain and the light chain of IgG immunoglobulins contain four framework regions (FR1 to FR4) which are separated in each case by three complementary-determining regions (CDR1 to CDR3). The CDRs and, in particular, the CDR3 regions and, still more particularly, the CDR3 region of the heavy chain are responsible to a large extent for antibody specificity.

Non-CDR regions of a mammalian antibody are known to be able to be replaced by similar regions of antibodies with the same or a different specificity, with the specificity for the epitope of the original antibody being retained. This made possible the development of "humanized" antibodies in which nonhuman CDRs are covalently linked to human FR and/or Fc/pFc' regions to produce a functional antibody.

As another example, WO 92/04381 describes the production and use of humanized murine RSV antibodies in which at least part of the murine FR regions have been replaced with FR regions of a human origin. Antibodies of this kind, including fragments of intact antibodies with antigen-binding capability, are often referred to as "chimeric" antibodies.

According to the invention, the term "antibody" also includes F(ab')$_2$, Fab, Fv, and Fd fragments of antibodies, chimeric antibodies, in which the Fc and/or FR and/or CDR1 and/or CDR2 and/or light chain-CDR3 regions have been replaced with homologous human or nonhuman sequences, chimeric F(ab')$_2$-fragment antibodies in which the FR and/or CDR1 and/or CDR2 and/or light chain-CDR3 regions have been replaced with homologous human or nonhuman sequences, chimeric Fab-fragment antibodies in which the FR and/or CDR1 and/or CDR2 and/or light chain-CDR3 regions have been replaced with homologous human or nonhuman sequences, and chimeric Fd-fragment antibodies in which the FR and/or CDR1 and/or CDR2 regions have been replaced with homologous human or nonhuman sequences. The term "antibody" also comprises "single-chain" antibodies.

Non-antibody proteins and peptides which bind specifically to tumor antigens may replace antibodies when used according to the invention. Binding substances of this kind may be provided, for example, by degenerate peptide libraries which may be prepared simply in solution in an immobilized form or as phage-display libraries. It is likewise possible to prepare combinatorial libraries of peptides with one or more amino acids. Libraries of peptoids and nonpeptidic synthetic residues may also be prepared.

Antibodies may also be coupled to a therapeutic label for displaying cells and tissues expressing tumor antigens. They may also be coupled to therapeutic effector moieties.

Detectable labels include any label that functions to: (i) provide a detectable signal; (ii) interact with a second label to modify the detectable signal provided by the first or second label, e.g. FRET (Fluorescence Resonance Energy Transfer); (iii) affect mobility, e.g. electrophoretic mobility, by charge, hydrophobicity, shape, or other physical parameters, or (iv) provide a capture moiety, e.g., affinity, antibody/antigen, or ionic complexation. Suitable as label are structures, such as fluorescent labels, luminescent labels, chromophore labels, radioisotopic labels, isotopic labels, preferably stable isotopic labels, isobaric labels, enzyme labels, particle labels, in particular metal particle labels, magnetic particle labels, polymer particle labels, small organic molecules such as biotin, ligands of receptors or binding molecules such as cell adhesion proteins or lectins, label-sequences comprising nucleic acids and/or amino acid residues which can be detected by use of binding agents, etc. Detectable labels comprise, in a nonlimiting manner, barium sulfate, iocetamic acid, iopanoic acid, calcium ipodate, sodium diatrizoate, meglumine diatrizoate, metrizamide, sodium tyropanoate and radio diagnostic, including positron emitters such as fluorine-18 and carbon-11, gamma emitters such as iodine-123, technetium-99m, iodine-131 and indium-111, nuclides for nuclear magnetic resonance, such as fluorine and gadolinium.

According to the invention, the term "therapeutic effector molecule" means any molecule which may exert a therapeutic effect. According to the invention, a therapeutic effector molecule is preferably selectively guided to a cell which expresses one or more tumor antigens and includes anticancer agents, radioactive iodine-labeled compounds, toxins, cytostatic or cytolytic drugs, etc. Anticancer agents comprise, for example, aminoglutethimide, azathioprine, bleomycin sulfate, busulfan, carmustine, chlorambucil, cisplatin, cyclophosphamide, cyclosporine, cytarabidine, dacarbazine, dactinomycin, daunorubin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

The term "major histocompatibility complex" or "MHC" includes MEW class I and class II and relates to a complex of genes present in all vertebrates. MEW proteins or molecules are involved in signaling between lymphocytes and antigen presenting cells in normal immune reactions by binding peptides and presenting them for recognition by T cell receptors (TCR). MEW molecules bind peptides within an intracellular processing compartment and present these peptides on the surface of antigen presenting cells for recognition by T cells. The human MEW region also termed HLA is located on chromosome 6 and includes the class I and class II region. In one preferred embodiment of all aspects of the invention an MHC molecule is an HLA molecule.

"Reduce" or "inhibit" as used herein means the ability to cause an overall decrease, preferably of 20% or greater, more preferably of 50% or greater, and most preferably of 75% or greater, in the level, e.g. in the level of protein or mRNA as compared to a reference sample (e.g., a sample not treated with siRNA). This reduction or inhibition of RNA or protein expression can occur through targeted mRNA cleavage or degradation. Assays for protein expression or nucleic acid expression are known in the art and include, for example, ELISA, western blot analysis for protein expression, and northern blotting or RNase protection assays for RNA.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

According to the invention the term "increased" or "increased amount" preferably refers to an increase by at least 10%, in particular at least 20%, at least 50% or at least 100%. The amount of a substance is also increased in a test sample such as a biological sample compared to a reference sample if it is detectable in the test sample but absent or not detectable in the reference sample.

According to the invention, the term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

Preferably, a tumor disease according to the invention is a cancer disease, i.e. a malignant disease and a tumor cell is a cancer cell. Preferably, a tumor disease or cancer disease is characterized by cells in which a tumor nucleic acid and/or tumor antigen identified according to the invention is expressed or abnormally expressed and/or a tumor cell or cancer cell is characterized by expression or abnormal expression of a tumor nucleic acid and/or tumor antigen identified according to the invention. Preferably, a tumor disease, a cancer disease, a tumor cell or a cancer cell is characterized by presentation of a tumor antigen identified according to the invention with class I MHC.

"Abnormal expression" means according to the invention that expression is altered, preferably increased, compared to the state in a healthy individual. An increase in expression refers to an increase by at least 10%, in particular at least 20%, at least 50%, at least 100%, at least 200%, at least 500%, at least 1000%, at least 10000% or even more. In one embodiment, expression is only found in a diseases tissue, while expression in a healthy tissue is repressed.

The term "tumor" according to the invention comprises tumor diseases of the central nervous system such as glioma, in particular glioblastoma. The term "cancer" according to the invention comprises cancer diseases of the central nervous system such as glioma, in particular glioblastoma.

The term "glioma" relates to a type of tumor that starts in the brain or spine. It is called a glioma because it arises from glial cells. The most common site of gliomas is the brain. Gliomas make up about 30% of all brain and central nervous system tumors and 80% of all malignant brain tumors.

Gliomas are named according to the specific type of cell they share histological features with, but not necessarily originate from. The main types of gliomas include ependymomas (ependymal cells), astrocytomas (astrocytes) (glioblastoma multiforme is a malignant astrocytoma and the most common primary brain tumor among adults), oligodendrogliomas (oligodendrocytes), brainstem glioma (develops in the brain stem), optic nerve glioma (develops in or around the optic nerve), and mixed gliomas (such as oligoastrocytomas, contain cells from different types of glia).

Treatment for brain gliomas depends on the location, the cell type and the grade of malignancy. Often, treatment is a combined approach, using surgery, radiation therapy, and chemotherapy. Spinal cord tumors can be treated by surgery and radiation. Temozolomide is a chemotherapeutic drug that is able to cross the blood-brain barrier effectively and is currently being used in therapy for high-grade tumors. Gliomas are rarely curable. The prognosis for patients with high-grade gliomas is generally poor, and is especially so for older patients. Glioblastoma multiforme has less than a 12-month average survival after diagnosis, though this has extended to 14 months with more recent treatments.

The term "Glioblastoma multiforme" (GBM), WHO classification name "glioblastoma", also known as Grade IV Astrocytoma, is the most common and most aggressive malignant primary brain tumor in humans, involving glial cells and accounting for 52% of all functional tissue brain tumor cases and 20% of all intracranial tumors. GBM presents two variants: giant cell glioblastoma and gliosarcoma.

Treatment can involve chemotherapy, radiation and surgery. Median survival with standard-of-care radiation and chemotherapy with temozolomide is 15 months. Median survival without treatment is 4½ months. Surgery remains the standard of care.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

According to the invention, a biological sample may be a tissue sample, including bodily fluids, and/or a cellular sample and may be obtained in the conventional manner such as by tissue biopsy, including punch biopsy, and by taking blood, bronchial aspirate, sputum, urine, feces or other body fluids. In one embodiment, a biological sample is a sample obtained from a tissue suspected of being affected with cancer. In one embodiment, a biological sample is a tumor sample, e.g. a sample obtained from a tumor and comprising tumor cells. According to the invention, the term "biological sample" also includes processed biological samples such as fractions or isolates of biological samples, e.g. nucleic acid and peptide/protein isolates.

The pharmaceutical compositions and methods of treatment described according to the invention may also be used for immunization or vaccination to therapeutically treat or prevent a disease described herein. According to the invention, the terms "immunization" or "vaccination" preferably relate to an increase in or activation of an immune response to an antigen. It is possible to use animal models for testing an immunizing effect on cancer. For example, human cancer cells may be introduced into a mouse to generate a tumor. The effect on the cancer cells (for example reduction in tumor size) may be measured as a measure for the effectiveness of an immunization by an agent administered to the animal.

As part of the composition for an immunization or a vaccination, preferably one or more agents as described herein are administered together with one or more adjuvants for inducing an immune response or for increasing an immune response. An adjuvant is a substance which enhances an immune response. Adjuvants may enhance the immune response by providing an antigen reservoir (extracellularly or in macrophages), activating macrophages and/or stimulating particular lymphocytes. Adjuvants are known and comprise in a nonlimiting way monophosphoryl lipid A (MPL, SmithKline Beecham), saponins such as QS21 (SmithKline Beecham), DQS21 (SmithKline Beecham; WO 96/33739), QS7, QS17, QS18 and QS-L1 (So et al., Mol. Cells 7:178-186, 1997), incomplete Freund's adjuvant, complete Freund's adjuvant, vitamin E, montanide, alum, CpG oligonucleotides (cf. Kreig et al., Nature 374:546-9, 1995) and various water-in-oil emulsions prepared from biologically degradable oils such as squalene and/or tocopherol. Preferably, according to the invention, peptides are administered in a mixture with DQS21/MPL. The ratio of DQS21 to MPL is typically about 1:10 to 10:1, preferably about 1:5 to 5:1 and in particular about 1:1. For administration to humans, a vaccine formulation typically contains DQS21 and MPL in a range from about 1 µg to about 100 µg.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (cf. Science 268:1432-1434, 1995), GM-CSF and IL-18.

There are a number of compounds which enhance an immune response and which therefore may be used in a vaccination. Said compounds comprise costimulating molecules provided in the form of proteins or nucleic acids such as B7-1 and B7-2 (CD80 and CD86, respectively).

Peptides may be administered in a manner known per se. In one embodiment, nucleic acids are administered by ex vivo methods, i.e. by removing cells from a patient, genetic modification of said cells in order to incorporate a nucleic acid and reintroduction of the altered cells into the patient. This generally comprises introducing a functional copy of a gene into the cells of a patient in vitro and reintroducing the genetically altered cells into the patient. The functional copy of the gene is under the functional control of regulatory elements which allow the gene to be expressed in the genetically altered cells. Transfection and transduction methods are known to the skilled worker.

The invention also provides for administering nucleic acids in vivo by using, for example, vectors such as viruses and target-controlled liposomes.

In a preferred embodiment, a virus or viral vector for administering a nucleic acid is selected from the group consisting of adenoviruses, adeno-associated viruses, pox viruses, including vaccinia virus and attenuated pox viruses, Semliki Forest virus, retroviruses, Sindbis virus and Ty virus-like particles. Particular preference is given to adenoviruses and retroviruses. The retroviruses are typically replication-deficient (i.e. they are incapable of generating infectious particles).

Methods of introducing nucleic acids into cells in vitro or in vivo comprise transfection of nucleic acid calcium phosphate precipitates, transfection of nucleic acids associated with DEAE, transfection or infection with the above viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g. a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively a tumor antigen. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

The therapeutically active compounds of the invention may be administered via any conventional route, including by injection or infusion. The administration may be carried out, for example, orally, intravenously, intraperitonealy, intramuscularly, subcutaneously or transdermally. Preferably, antibodies are therapeutically administered by way of a lung aerosol. Antisense nucleic acids are preferably administered by slow intravenous administration.

The compositions of the invention are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. According to the invention, a diagnosis or treatment of cancer may also include the diagnosis or treatment of cancer metastases which have already formed or will form. According to the invention, the term "treatment" comprises therapeutic and prophylactic treatment, i.e. prevention.

An effective amount of a composition of the invention will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses of the compositions of the invention administered may depend on various of such parameters. In the case that a reaction in a patient is insufficient with an initial dose, higher doses (or effectively higher doses achieved by a different, more localized route of administration) may be used.

The pharmaceutical compositions of the invention are preferably sterile and contain an effective amount of the therapeutically active substance to generate the desired reaction or the desired effect.

Generally, doses of a peptide of from 1 ng to 1 mg, preferably from 10 ng to 100 µg, are formulated and administered. If the administration of nucleic acids (DNA and RNA) is desired, doses of from 1 ng to 0.1 mg may be formulated and administered.

The pharmaceutical compositions of the invention are generally administered in pharmaceutically compatible amounts and in pharmaceutically compatible preparation. The term "pharmaceutically compatible" refers to a nontoxic material which does not interact with the action of the active component of the pharmaceutical composition. Preparations of this kind may usually contain salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a nonlimiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. The term "carrier" refers to an organic or inorganic component, of a natural or synthetic nature, in which the active component is combined in order to facilitate application. According to the invention, the term "pharmaceutically compatible carrier" includes one or more compatible solid or liquid fillers, diluents or encapsulating substances, which are suitable for administration to a patient. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1: Expression of COL20A1 in different tumor tissues
COL20A1 expression was analysed using quantitative real time PCR with primers 6303 (5'-TTCACGCTCT-TCAAGGACGC) and 6304 (5'-TGGAAGTCCTCGGCT-GTCAT) in the indicated tumors tissues and the relative expression was calculated using HPRT (Hypoxanthine-guanine phosphoribosyltransferase) as housekeeping gene. Brain tumor refers to Glioblastoma, TNBC refers to Triple negative breast cancer.

Figure 2:
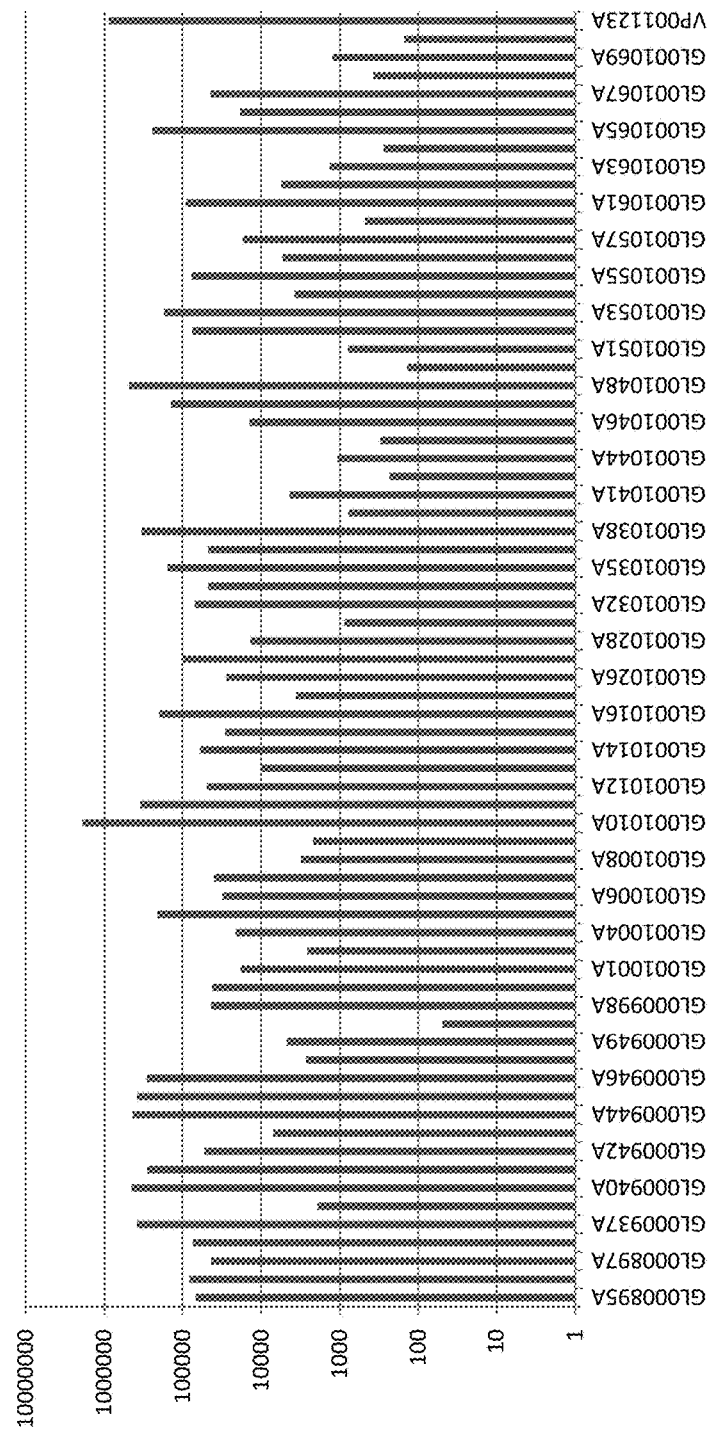

FIG. 2: Expression of COL20A1 in glioblastoma tissues
COL20A1 expression was analysed using quantitative real time PCR with primers 6303 (5'-TTCACGCTCT-TCAAGGACGC) and 6304 (5'-TGGAAGTCCTCGGCT-GTCAT) in 71 glioblastoma tissues and the relative expression was calculated using HPRT (Hypoxanthine-guanine phosphoribosyltransferase) as housekeeping gene.

FIG. 3: Expression of COL20A1 in normal tissues
Expression height is color coded for a number of discrete expression levels (see color code above the figure).

FIG. 4: Homology of COL20A1 to others proteins
A. Homology of COL20A1 to other collagens proteins was assessed by Blastp using as reference the NCBI Protein Reference Sequences. B. Homology of COL20A1 to COL14A1. Homology of COL20A1 to COL14A1 was assessed by Blastp showing no identical consecutive protein sequence.

FIG. 5: Predicted HLA-A*02:01 T-Cell epitopes of COL20A1

HLA-A*02:01 T-Cell epitopes were predicted using SYF-PEITHI, only TCR epitopes with a score more than 20 and unique for COL20A1 are shown.

Figure 6:
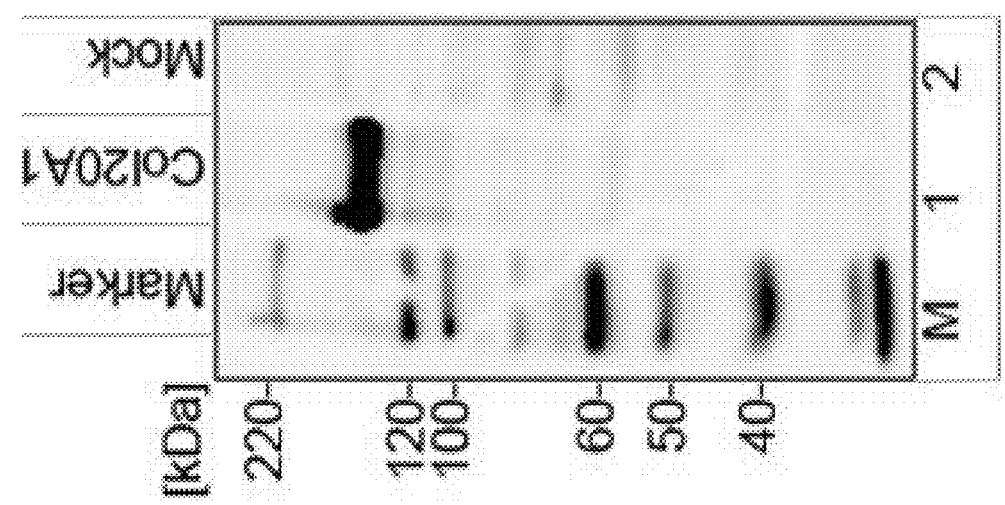

FIG. 6: COL20A1 mRNA can be translated from human cells

HEK-293 T cells were transfected with a vector containing the sequence coding for COL20A1 (lane1) or with vector alone (lane2).

EXAMPLES

The techniques and methods used herein are described herein or carried out in a manner known per se and as described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information unless specifically indicated.

Example 1: COL20A1 is a Highly Specific Biomarker for Glioblastoma

To verify the specificity of COL20A1 for glioblastoma, RNA was extracted from normal tissues or glioblastoma samples using an extraction kit for lipid-rich tissues. cDNA synthesis was performed using MMLV Reverse Transcriptase and random timers/oligo dT primers. COL20A1 expression was analysed using quantitative real time PCR with primers 6303 (5'-TTCACGCTCTTCAAGGACGC) and 6304 (5'-TGGAAGTCCTCGGCTGTCAT) and the relative expression was calculated using HPRT (Hypoxanthine-guanine phosphoribosyltransferase) as housekeeping gene.

This method is used for analysis the expression of COL20A1 in 13 different tumour entities (FIG. 1). Only glioblastoma (labeled as brain tumors in FIG. 1) show a strong expression of COL20A1, while all other tumour entities show no or very low expression of COL20A1, with the exception of few samples in testis cancer. As shown in FIG. 2, the transcript COL20A1 (NM_020882.2, NP_065933.2) is highly expressed in 50% of analysed glioblastomas if a cut off of 40000 is used, suggesting that a large number of GBM patients would benefit from a treatment targeting COL20A1. The tumor specificity of the transcript was analysed by said qRT-PCR protocol in a large set of normal tissues (n=65). COL20A1 is weekly expressed in some adult brain regions and spinal cord (FIG. 3). In contrast, ERBB2, a generally accepted target of vaccination and other immunotherapeutic approaches, shows a high expression (relative expression more than 40000) in several normal tissues, including some brain areals (FIG. 3).

Example 2: Low Homology Limits Expected Cross Reactivity of Other Collagen Family Members The human COL20A1 open reading frame encodes a 1284 amino acid protein with a predicted molecular weight of 136 kDa. A 22 amino acid signal sequence is predicted. Homology of COL20A1 to other collagen proteins was assessed by Blast showing that the overall homology to other collagens is low, with the highest alignment score found with the collagen alpha-1(XIV) (COL14A1) and collagen alpha-1(XII) (COL12A1) (FIG. 4A). Importantly, no long stretches of amino acids are identical between COL20A1 and other collagens as showed in FIG. 4B for COL14A1 suggesting that COL20A1 can therefore be used for specific targeting and detection of the molecule (FIG. 4B).

Example 3: COL20A1 Specific Sequences Contain Predicted T Cell Epitopes

To address the targetability of COL20A1 by CD8+T-lymphocytes, HLA-A*02:01 epitopes present on the sequence were predicted using the SYFPEITHI database. 58 HLA-A*02:01 epitopes unique for COL20A1 were detected (FIG. 5) suggesting that COL20A1 could be used for T-cell based therapy.

Example 4: COL20A1 mRNA can be Translated from Human Cells

A recombinant sequence coding for COL20A1 was transfected into HEK-293 T cells and cell lysates were analysed by Western Blot with a commercial available COL20A1 specific antibody (Sigma). A band of the expected COL20A1 size can be detected in the transfected cells but not in the mock transfected cells indicating that the COL20A1 mRNA can be translated to a stable protein in human cells (FIG. 6).

The invention claimed is:

1. A method for diagnosis, detection or monitoring of a glioblastoma characterized by expression of a tumor antigen, the method comprising the detection of and/or determination of the quantity of one or more parameters selected from the group consisting of:

(i) a nucleic acid which codes for said tumor antigen or a tumor antigen peptide derived from said tumor antigen, (ii) a peptide comprising the amino acid sequence of said tumor antigen or of a tumor antigen peptide derived from said tumor antigen, (iii) an antibody which binds to a peptide comprising the amino acid sequence of said tumor antigen or of a tumor antigen peptide derived from said tumor antigen, (iv) a T cell that recognizes a peptide comprising the amino acid sequence of said tumor antigen or of a tumor antigen peptide derived from said tumor antigen, and (v) a cell which presents a peptide comprising the amino acid sequence of said tumor antigen peptide derived from a tumor antigen, in a biological sample isolated from a patient, wherein said tumor antigen comprises an amino acid sequence encoded by a nucleic acid which comprises the nucleic acid sequence according to SEQ ID NO: 1 or 2 of the sequence listing and said tumor antigen peptide comprises an amino acid sequence corresponding to the amino acid sequence of a fragment of said tumor antigen, wherein said tumor antigen peptide comprises at least 6 consecutive amino acids of said tumor antigen, wherein the presence of the nucleic acid, peptide, antibody, T cell, or cell in the biological sample or an increased quantity of the nucleic acid, peptide, antibody, T cell, or cell in the biological sample compared to a reference level is indicative of glioblastoma.

2. The method as claimed in claim 1, wherein the biological sample is from a tissue or organ wherein the cells when the tissue or organ is free of tumors do not substantially express said tumor antigen and/or a nucleic acid encoding said tumor antigen.

3. The method as claimed in claim 1, wherein the detection and/or determination of the quantity comprises:
 (i) contacting the biological sample with an agent which binds specifically to the nucleic acid, the peptide, the antibody, the T cell or the cell which is to be detected and/or the quantity of which is to be determined, and
 (ii) detecting the formation of and/or determining the quantity of a complex between the agent and the nucleic acid, the peptide, the antibody, the T cell or the cell which is to be detected or the quantity of which is to be determined.

4. The method as claimed in claim 3, wherein (i) the agent which binds specifically to the nucleic acid comprises an oligonucleotide, which hybridizes specifically to said nucleic acid, (ii) the agent which binds specifically to the peptide comprises an antibody binding specifically to said peptide, (iii) the agent which binds specifically to the antibody comprises a peptide binding specifically to said antibody, or (iv) the agent which binds specifically to the T cell comprises a cell presenting a complex between an MHC molecule and the peptide comprising the amino acid sequence of a tumor antigen peptide derived from said tumor antigen.

5. The method as claimed in claim 3, wherein the agent further comprises a detectable label.

6. A method for detecting expression or activity of COL20A1 in a patient suspected of having glioblastoma or having a potential for developing glioblastoma, the method comprising:
 (i) obtaining a biological sample from the patient;
 (ii) detecting or quantifying (a) a nucleic acid which codes for a COL20A1 protein or a fragment thereof, or (b) COL20A1 protein or a fragment thereof in the sample, wherein the COL20A1 protein has an amino acid sequence of SEQ ID NO: 3 or SEQ ID NO: 4 and wherein the fragment comprises at least 6 consecutive amino acids of the COL20A1 protein.

7. The method as claimed in claim 6, wherein step (ii) comprises: contacting the biological sample with an agent which binds specifically to the nucleic acid and detecting the formation of and/or determining the quantity of a complex between the agent and the nucleic acid.

8. The method as claimed in claim 7, wherein the agent which binds specifically to the nucleic acid comprises an oligonucleotide that hybridizes specifically to the nucleic acid.

9. The method as claimed in claim 8, wherein the oligonucleotide comprises a detectable label.

10. The method as claimed in claim 6, wherein step (ii) comprises: contacting the biological sample with an agent which binds specifically to the protein or fragment thereof and detecting the formation of and/or determining the quantity of a complex between the agent and the protein or fragment thereof.

11. The method as claimed in claim 10, wherein the agent which binds specifically to the protein or fragment thereof comprises an antibody.

12. The method as claimed in claim 11, wherein the antibody comprises a detectable label.

13. The method as claimed in claim 6, wherein the patient has glioblastoma.

\* \* \* \* \*